(12) United States Patent
Almstead et al.

(10) Patent No.: US 9,309,206 B2
(45) Date of Patent: Apr. 12, 2016

(54) CRYSTALLINE FORMS OF 3-[5-(2-FLUOROPHENYL)-[1,2,4] OXADIAZOL-3-YL]-BENZOIC ACID

(71) Applicant: PTC Therapeutics, Inc., South Plainfield, NJ (US)

(72) Inventors: Neil G. Almstead, Princeton, NJ (US); Peter Seongwoo Hwang, Edison, NJ (US); Young-Choon Moon, Belle Mead, NJ (US)

(73) Assignee: PTC Therapeutics, Inc., South Plainfield, NJ (US)

( * ) Notice: Subject to any disclaimer, the term of this patent is extended or adjusted under 35 U.S.C. 154(b) by 0 days.

(21) Appl. No.: 14/261,774

(22) Filed: Apr. 25, 2014

(65) Prior Publication Data

US 2014/0235679 A1    Aug. 21, 2014

Related U.S. Application Data

(60) Continuation of application No. 13/764,807, filed on Feb. 12, 2013, now Pat. No. 8,748,625, which is a continuation of application No. 12/913,213, filed on Oct. 27, 2010, now Pat. No. 8,394,966, which is a division of application No. 11/904,005, filed on Sep. 24, 2007, now Pat. No. 7,863,456.

(60) Provisional application No. 60/847,326, filed on Sep. 25, 2006.

(51) Int. Cl.
*A61K 31/41* (2006.01)
*C07D 271/06* (2006.01)

(52) U.S. Cl.
CPC .................................. *C07D 271/06* (2013.01)

(58) Field of Classification Search
USPC ......................................................... 514/364
See application file for complete search history.

(56) References Cited

U.S. PATENT DOCUMENTS

| | | | |
|---|---|---|---|
| 6,660,753 B2 | 12/2003 | Van Wagenen et al. | |
| 6,759,538 B2 | 7/2004 | Singh et al. | |
| 6,992,096 B2 | 1/2006 | Karp et al. | |
| 7,041,685 B2 | 5/2006 | Cai et al. | |
| 7,112,595 B2 | 9/2006 | Van Wagenen et al. | |
| 7,153,880 B2 | 12/2006 | Singh et al. | |
| 7,202,262 B2 | 4/2007 | Karp et al. | |
| 7,419,991 B2 | 9/2008 | Karp et al. | |
| 7,678,922 B2 | 3/2010 | Almstead et al. | |
| 7,772,259 B2 * | 8/2010 | Karp et al. | 514/364 |
| 7,799,782 B2 * | 9/2010 | Munson et al. | 514/234.5 |
| 8,129,540 B2 | 3/2012 | Karp et al. | |
| 8,227,494 B2 | 7/2012 | Karp et al. | |
| 8,374,966 B1 * | 2/2013 | Arora et al. | 705/52 |
| 8,716,321 B2 * | 5/2014 | Hirawat et al. | 514/364 |
| 8,796,322 B2 * | 8/2014 | Karp et al. | 514/364 |
| 2004/0132726 A1 | 7/2004 | Arora et al. | |
| 2004/0204461 A1 * | 10/2004 | Karp et al. | 514/364 |
| 2005/0075375 A1 | 4/2005 | Vourloumis et al. | |
| 2005/0164973 A1 | 7/2005 | Karp et al. | |
| 2006/0089365 A1 | 4/2006 | Hintermann et al. | |
| 2006/0148863 A1 | 7/2006 | Karp et al. | |
| 2006/0148864 A1 | 7/2006 | Karp et al. | |
| 2007/0161687 A1 | 7/2007 | Karp et al. | |
| 2008/0171377 A1 | 7/2008 | Almstead et al. | |
| 2012/0277234 A1 | 11/2012 | Karp et al. | |

FOREIGN PATENT DOCUMENTS

WO    WO 2006/110483    10/2006

OTHER PUBLICATIONS

Brittain's, 1999, pp. 348-361.*
Wikipedia, metabolites and metabolism, 2005.*
U.S. Appl. No. 60/269,847, filed Feb. 21, 2001, Van Wagenen et al.
U.S. Appl. No. 60/149,464, filed Aug. 19, 1999, Van Wagenen et al.
U.S. Appl. No. 60/405,472, filed Aug. 23, 2002, Singh et al.
U.S. Appl. No. 60/350,107, filed Nov. 2, 2001, Singh et al.
Knapman, 2000, "Polymorphic predictions—Understanding the nature of crystalline compounds can be critical in drug development and manufacture," Modern Drug Discovery, Mar. 2000, pp. 53-57.
Welch et al., 2007, "PTC124 Targets Genetic Disorders Caused by Nonsense Mutations," *Nature* 447:87-91.
Supplementary Information from Welch et al., 2007, "PTC124 Targets Genetic Disorders Caused by Nonsense Mutations," *Nature* 447:87-91 (pp. 1-23).
Hirawat et al., 2007, "Safety, Tolerability, and Pharmacokinetics of PTC124, a Nonaminoglycoside Nonsense Mutation Suppressor, Following Single- and Multiple-Dose Administration to Healthy Male and Female Adult Volunteers," *Journal of Clinical Pharmacology* 47(4):430-444.
Du et al., 2008, "PTC124 is an orally bioavailable compound that promotes suppression of the human CFTR-G542X nonsense allele in a CF mouse model." *PNAS* 105(6):2064-2069.
Kerem et al., 2008, "Effectiveness of PTC124 treatment of cystic fibrosis caused by nonsense mutations: a prospective phase II trial," *The Lancet* 372:719-27.
Auld et al., 2009, "Mechanism of PTC124 activity in cell based luciferase assays of nonsense codon suppression," *PNAS Early Edition*:1-6 (document sent via fax Jan. 28, 2009).
Auld et al., 2009, "Mechanism of PTC124 activity in cell based luciferase assays of nonsense codon suppression," *PNAS Early Edition*:1-6 (document previously available from www.genome.gov website in Feb. 2008).
Auld et al., 2009, "Mechanism of PTC124 activity in cell based luciferase assays of nonsense codon suppression," *PNAS Early Edition*:1-6.

(Continued)

*Primary Examiner* — Rei-Tsang Shiao
(74) *Attorney, Agent, or Firm* — Jones Day

(57) ABSTRACT

The present invention relates to crystalline forms of 3-[5-(2-fluorophenyl)-[1,2,4]oxadiazol-3-yl]-benzoic acid, pharmaceutical compositions and dosage forms comprising the crystalline forms, methods of making the crystalline forms and methods for their use for the treatment, prevention or management of diseases ameliorated by modulation of premature translation termination or nonsense-mediated mRNA decay.

11 Claims, 11 Drawing Sheets

(56) References Cited

OTHER PUBLICATIONS

Figure 1:
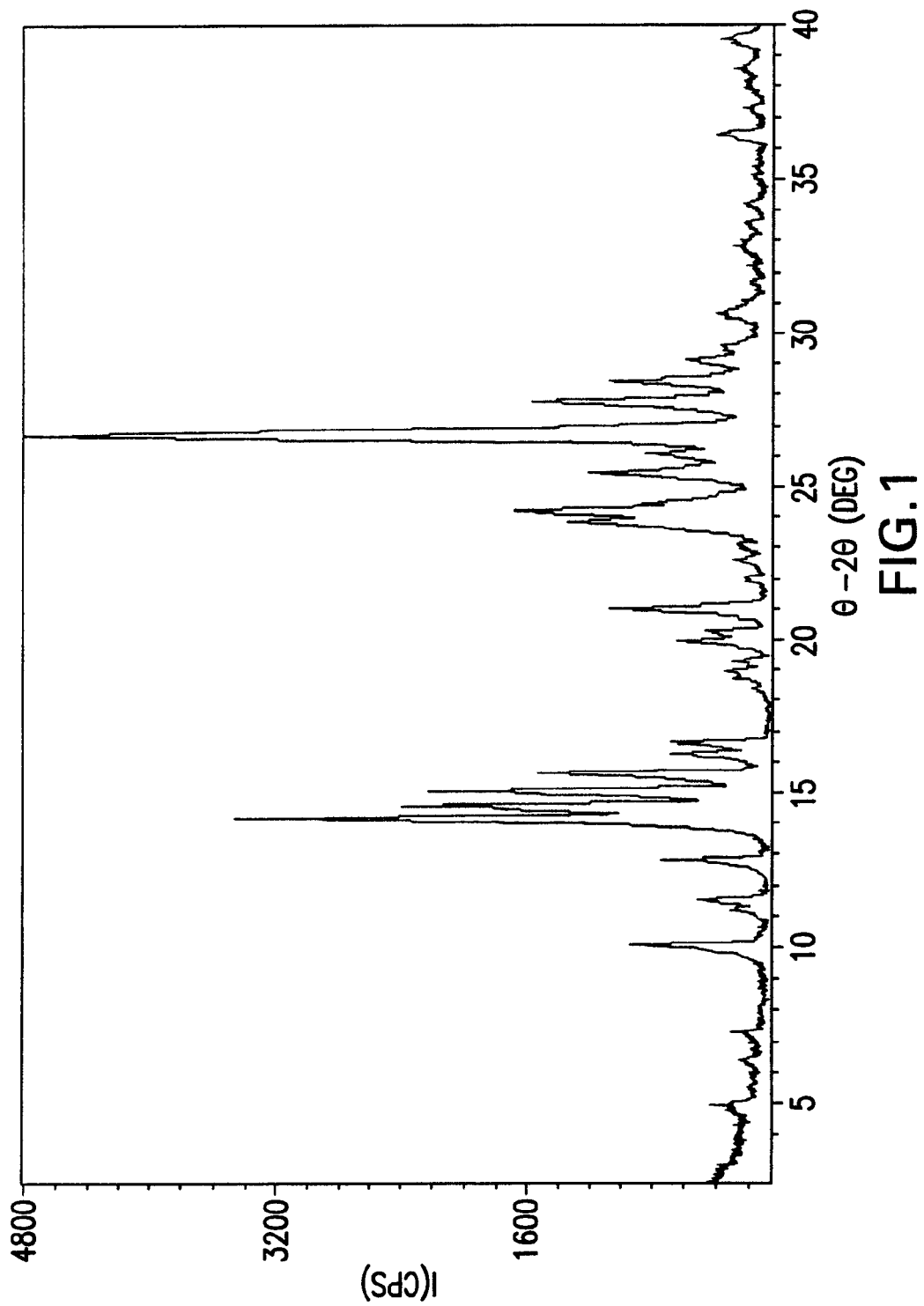

Supplemental Information Methods from Auld et al., 2009, "Mechanism of PTC124 activity in cell based luciferase assays of nonsense codon suppression," *PNAS Early Edition*:1-6 (pp. 1-17).

Announcement by PTC Therapeutics, Inc. and Genzyme Corporation dated Mar. 3, 2010.

Auld et al., 2010, "Molecular basis for the high-affinity binding and stabilization of firefly luciferase by PTC124," *PNAS* 107(11):4878-4883.

Braga and Grepioni, 2005, "Making crystals from crystals: a green route to crystal engineering and polymorphism," *Chem. Commun.*:3635-3645.

Jones et al., 2006, Pharmaceutical Cocrystals: an Emerging Approach to Physical Property Enhancement, *MRS Bulletin* 31:875-879.

Price, 2004, "The computational prediction of pharmaceutical crystal structures and polymorphism," *Advanced Drug Delivery Reviews* 56:301-319.

Bernstein, 2004, "Crystal Structure Prediction and Polymorphism," *ACA Transactions* 39:14-23.

Au et al., 1998, "Germ-Line Mutational Analysis of the TSC2 Gene in 90 Tuberouse-Sclerosis Patients," *Am. J. Hum. Genet.* 62:286-294.

Gite et al., 2003, "A high-throughput nonisotopic protein truncation test" *Nature Biotechnology* 21:194-197.

Guillonneau et al., 1999, "A nonsense mutation in a novel gene is associated with retinities pigmentosa in a family linked to the RP1 locus" *Human Molecular Genetics* 8:1541-1546.

Koeberl et al., 1990, "Recurrent nonsense mutations at arginine residues cause severe hemophilia B in unrelated hemophiles" *Hum. Genet.* 84:387-390.

Laake et al., 2000, "Characterization of *ATM* Mutations in 41 Nordic Families With Ataxia Telangiectasia" *Human Mutation* 16:232-246.

James et al., 2005, "Aminoglycoside suppression of nonsense mutations in severe hemophilia" *Hemostasis, Thrombosis, and Vascular Biology*:106(9):3043-3048.

Hein et al., 2004, "alpha-L-iduronidase premature stop codons and potential read-through in mucopolysaccharidosis type I patients" *J Mol. Biol.* 338(3):453-462.

Schrijver et al., 2002, "Premature Termination Mutations in *FBN1*: Distinct Effects on Differential Allelic Expression and on Protein and Clinical Phenotypes" *Am. J. Hum. Genet.* 71:223-237.

Yogalingam et al., 2001, "Molecular Genetics of Mucopolysaccharidosis Type IIIA and IIIB: Diagnostic, Clinical, and Biological Implications" *Human Mutation* 18:264-281.

Wakamatsu et al., 1999, "Mutations producing premature termination of translation and an amino acid substitution in the sterol 27-hydroxylase gene cause cerebrotendinous xanthomatosis associated with parkinsonism" *J. Neurol. Neurosurg. Psychiaatry* 67:195-198.

Jones et al., 1999, "Comprehensive Mutation Analysis of TSC1 and TSC2—and Phenotypic Correlations in 150 Families with Tuberous Sclerosis," *Am. J. Hum. Genet.* 64:1305-1315.

Strizheva et al., 2001, "The Spectrum of Mutations in TSC1 and TSC2 in Women with Tuberous Sclerosis and Lymphangiomyomatosis," *Am. J. Respir. Crit. Care Med.* 163:253-258.

Tzoulaki et al., 2005, "PAX6 mutations: genotype-phenotype correlations" *BMC Genetics* 6(27):1-12.

\* cited by examiner

CRYSTALLINE FORMS OF 3-[5-(2-FLUOROPHENYL)-[1,2,4]OXADIAZOL-3-YL]-BENZOIC ACID

This application is a continuation of U.S. application Ser. No. 13/764,807, filed Feb. 12, 2013, currently allowed, which is a continuation of U.S. application Ser. No. 12/913,213, filed Oct. 27, 2010, now U.S. Pat. No. 8,394,966, issued Mar. 12, 2013, which is a division of U.S. application Ser. No. 11/904,005, filed Sep. 24, 2007, now U.S. Pat. No. 7,863,456, issued Jan. 4, 2011, which claims the benefit of U.S. provisional application No. 60/847,326, filed Sep. 25, 2006, each of which is incorporated by reference herein in its entirety.

1. FIELD

The present invention relates to crystalline forms of the compound 3-[5-(2-fluorophenyl)-[1,2,4]oxadiazol-3-yl]-benzoic acid, pharmaceutical dosage forms and compositions comprising the crystalline forms, methods of making the crystalline forms and methods for their use for the treatment, prevention and management of diseases ameliorated by modulation of premature translation termination or nonsense-mediated mRNA decay.

2. BACKGROUND 1,2,4-oxadiazole compounds useful for the treatment, prevention or management of diseases ameliorated by modulation of premature translation termination or nonsense-mediated mRNA decay as described in U.S. Pat. No. 6,992,096 B2, issued Jan. 31, 2006, which is incorporated herein by reference in its entirety. One such compound is 3-[5-(2-fluorophenyl)-[1,2,4]oxadiazol-3-yl]-benzoic acid.

Solid forms such as salts, crystal forms, e.g., polymorphic forms of a compound are known in the pharmaceutical art to affect, for example, the solubility, stability, flowability, fractability, and compressibility of the compound as well as the safety and efficacy of drug products based on the compound, (see, e.g., Knapman, K. *Modern Drug Discoveries*, 2000:53). So critical are the potential effects of solid forms in a single drug product on the safety and efficacy of the respective drug product that the United States Food and Drug Administration requires the identification and control of solid forms, e.g., crystalline forms of each compound used in each drug product marketed in the United States. Accordingly, new crystalline forms of 1,2,4-oxadiazole benzoic acids can further the development of formulations for the treatment, prevention or management of disease ameliorated by modulation of premature translation termination or nonsense-mediated mRNA decay. The present invention provides such novel crystalline forms, for example, crystalline forms of 3-[5-(2-fluorophenyl)-[1,2,4]oxadiazol-3-yl]-benzoic acid.

Citation of any reference in Section 2 of this application is not to be construed as an admission that such reference is prior art to the present application.

3. SUMMARY

The invention provides novel crystalline forms of 3-[5-(2-fluorophenyl)-[1,2,4]oxadiazol-3-yl]-benzoic acid, which has the following chemical structure (I):

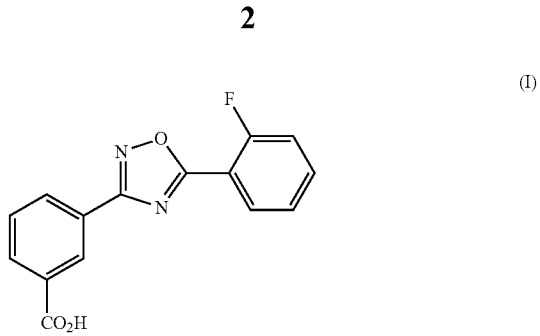

In particular, crystalline forms of 3-[5-(2-fluorophenyl)-[1,2,4]oxadiazol-3-yl]-benzoic acid are useful for the treatment, prevention or management of diseases ameliorated by modulation of premature translation termination or nonsense-mediated mRNA decay, said diseases being described in U.S. Pat. No. 6,992,096 B2, issued Jan. 31, 2006, which is incorporated herein by reference in its entirety. In addition, the present provides a crystalline form of 3-[5-(2-fluorophenyl)-[1,2,4]oxadiazol-3-yl]-benzoic acid which is substantially pure, i.e., its purity greater than about 90%.

Certain embodiments of the invention provide pharmaceutical dosage forms and compositions comprising a crystalline form of 3-[5-(2-fluorophenyl)-[1,2,4]oxadiazol-3-yl]-benzoic acid and a pharmaceutically-acceptable diluent, excipient or carrier. The invention further provides methods of their use for the treatment, prevention or management of diseases ameliorated by modulation of premature translation termination or nonsense-mediated mRNA decay. In certain embodiments, the invention provides methods of making, isolating and/or characterizing the crystalline forms of the invention. The crystalline forms of the invention are useful as active pharmaceutical ingredients for the preparation of formulations for use in animals or humans. Thus, the present invention encompasses the use of these crystalline forms as a final drug product. The crystalline forms and final drug products of the invention are useful, for example, for the treatment, prevent or management of the diseases described herein.

4. DETAILED DESCRIPTION OF THE INVENTION

4.1 Brief Description of the Drawings

FIG. 1 provides an X-ray powder diffraction (XRPD) pattern of a sample comprising Form A of 3-[5-(2-fluorophenyl)-[1,2,4]oxadiazol-3-yl]-benzoic acid.

Figure 2:
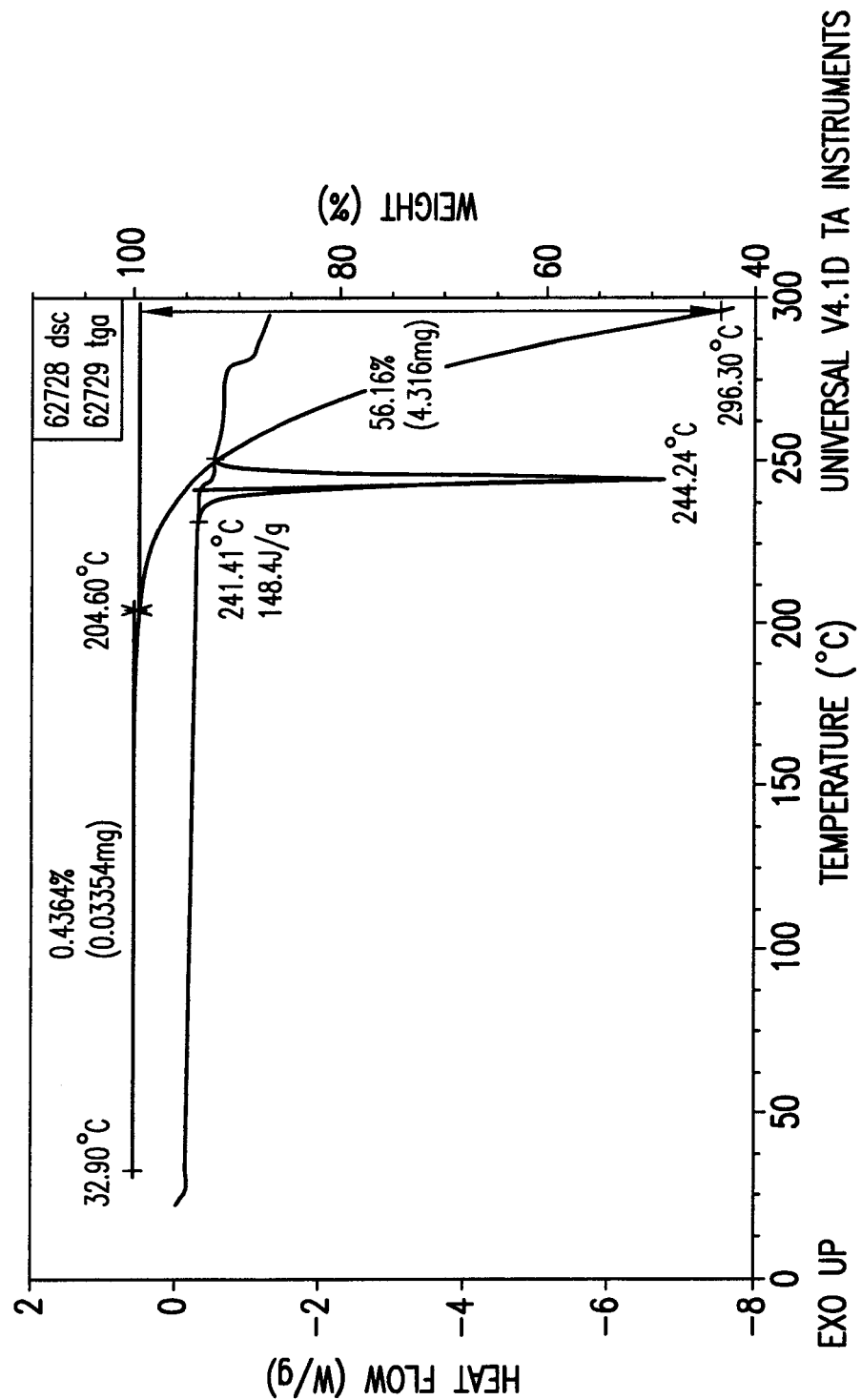

FIG. 2 provides differential scanning calorimetry (DSC) and thermogravimetric analysis (TGA) thermograms of a sample comprising Form A of 3-[5-(2-fluorophenyl)-[1,2,4]oxadiazol-3-yl]-benzoic acid.

Figure 3:
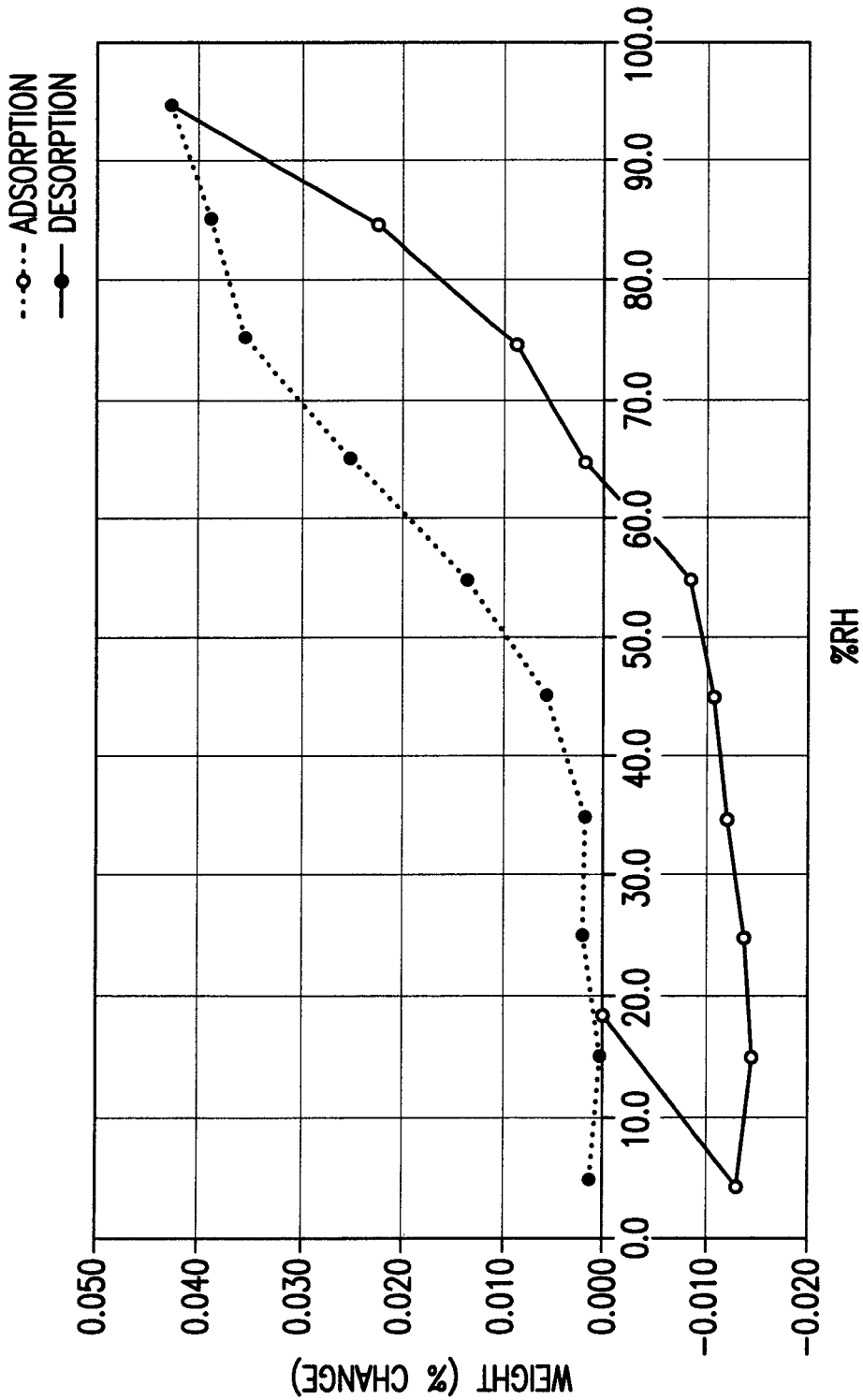

FIG. 3 provides a dynamic vapor sorption (DVS) isotherm of a sample comprising Form A of 3-[5-(2-fluorophenyl)-[1,2,4]oxadiazol-3-yl]-benzoic acid.

Figure 4:
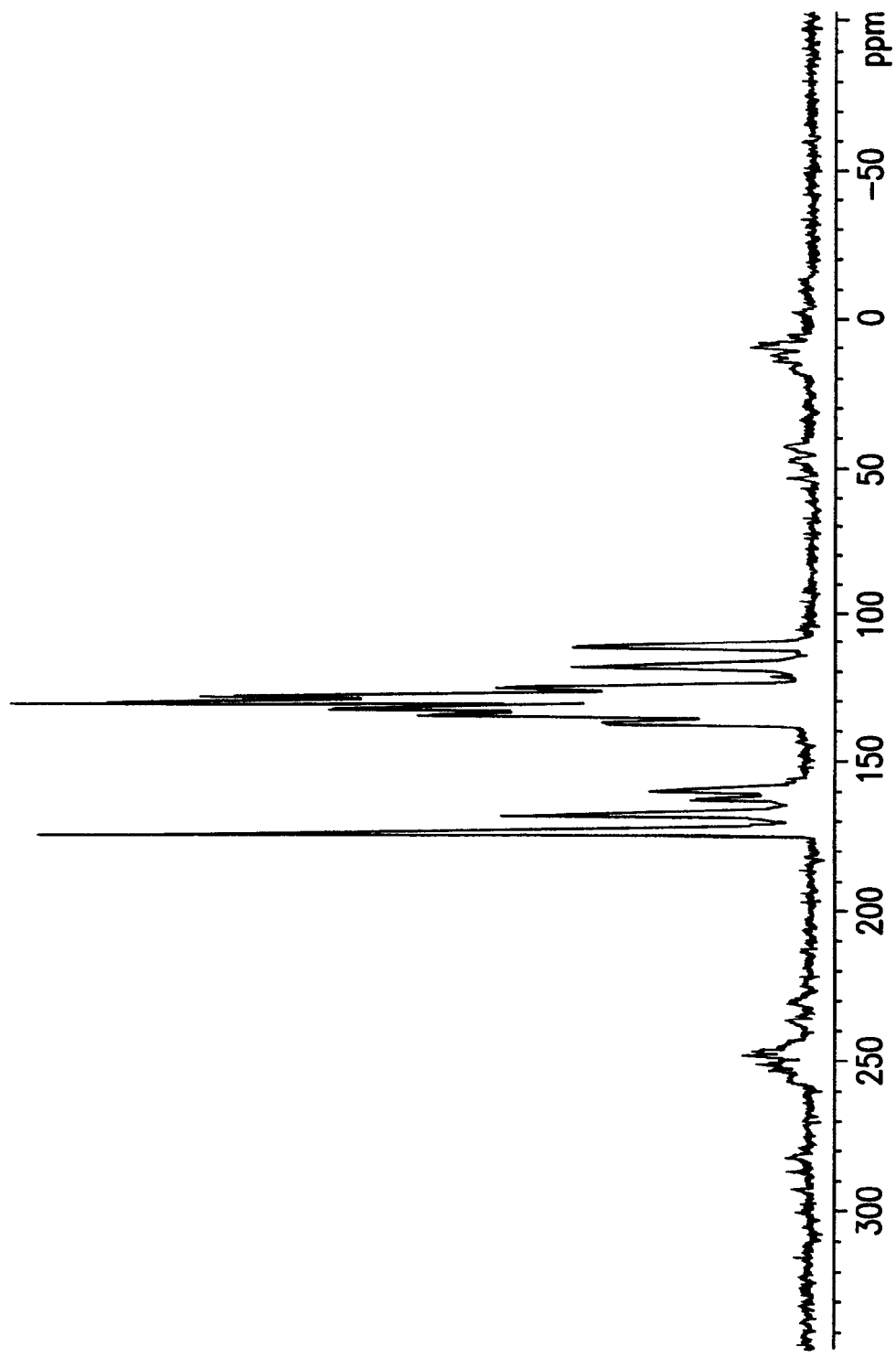

FIG. 4 provides a solid-state $^{13}C$ NMR spectrum of a sample comprising Form A of 3-[5-(2-fluorophenyl)-[1,2,4]oxadiazol-3-yl]-benzoic acid.

Figure 5:
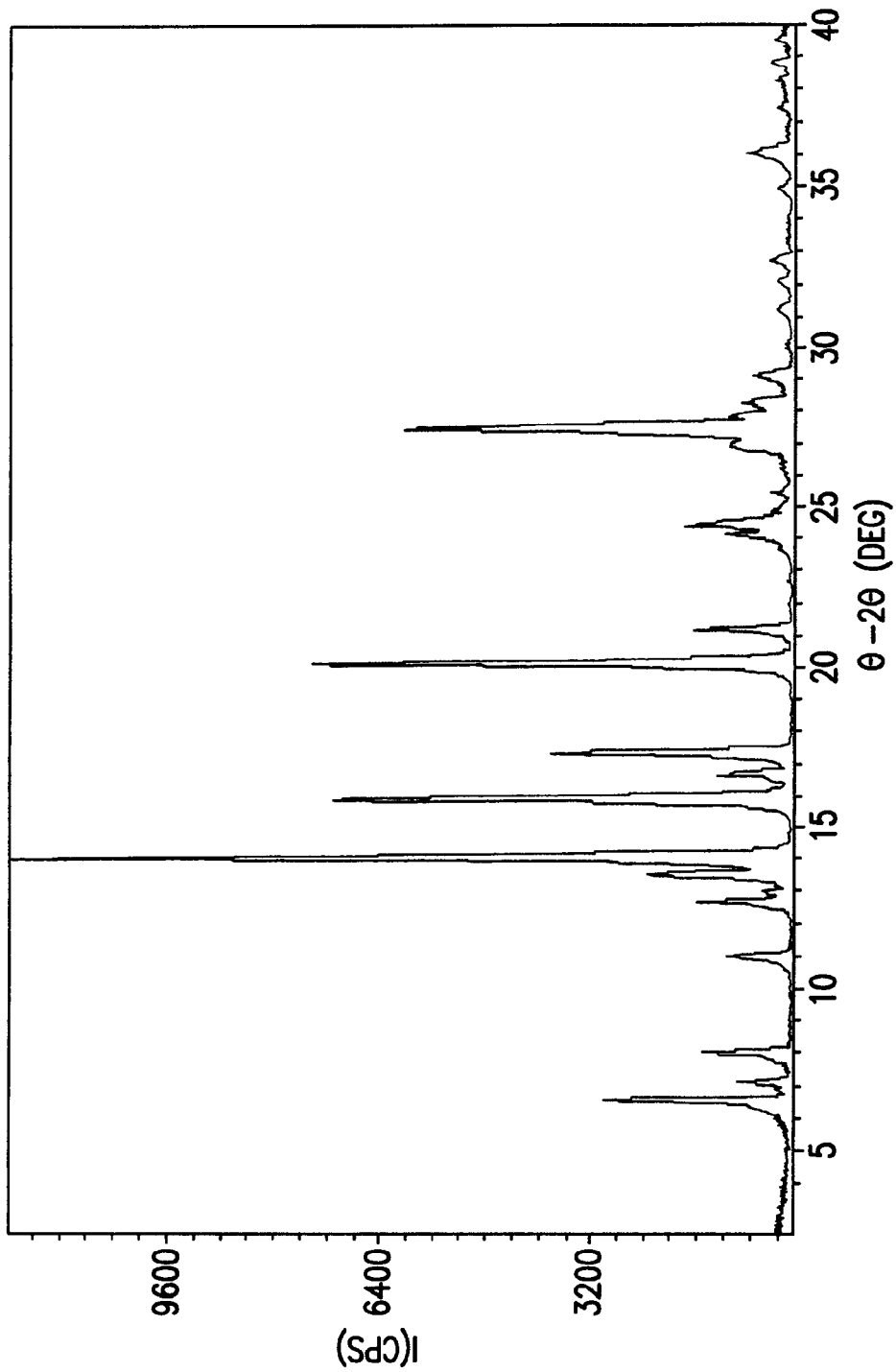

FIG. 5 provides a XRPD pattern of a sample comprising Form B of 3-[5-(2-fluorophenyl)-[1,2,4]oxadiazol-3-yl]-benzoic acid.

Figure 6:
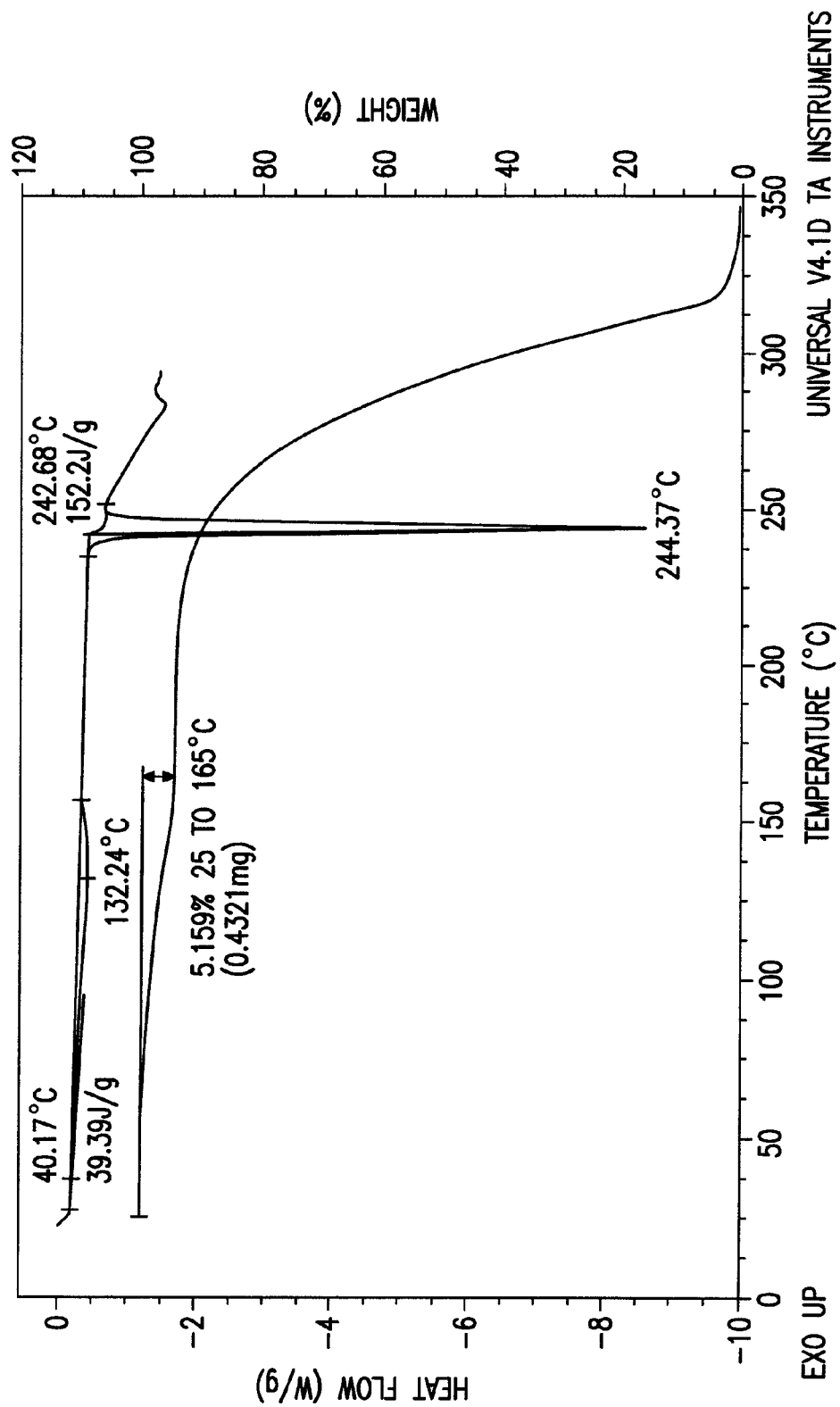

FIG. 6 provides DSC and TGA thermograms of a sample comprising Form B of 3-[5-(2-fluorophenyl)-[1,2,4]oxadiazol-3-yl]-benzoic acid.

Figure 7:
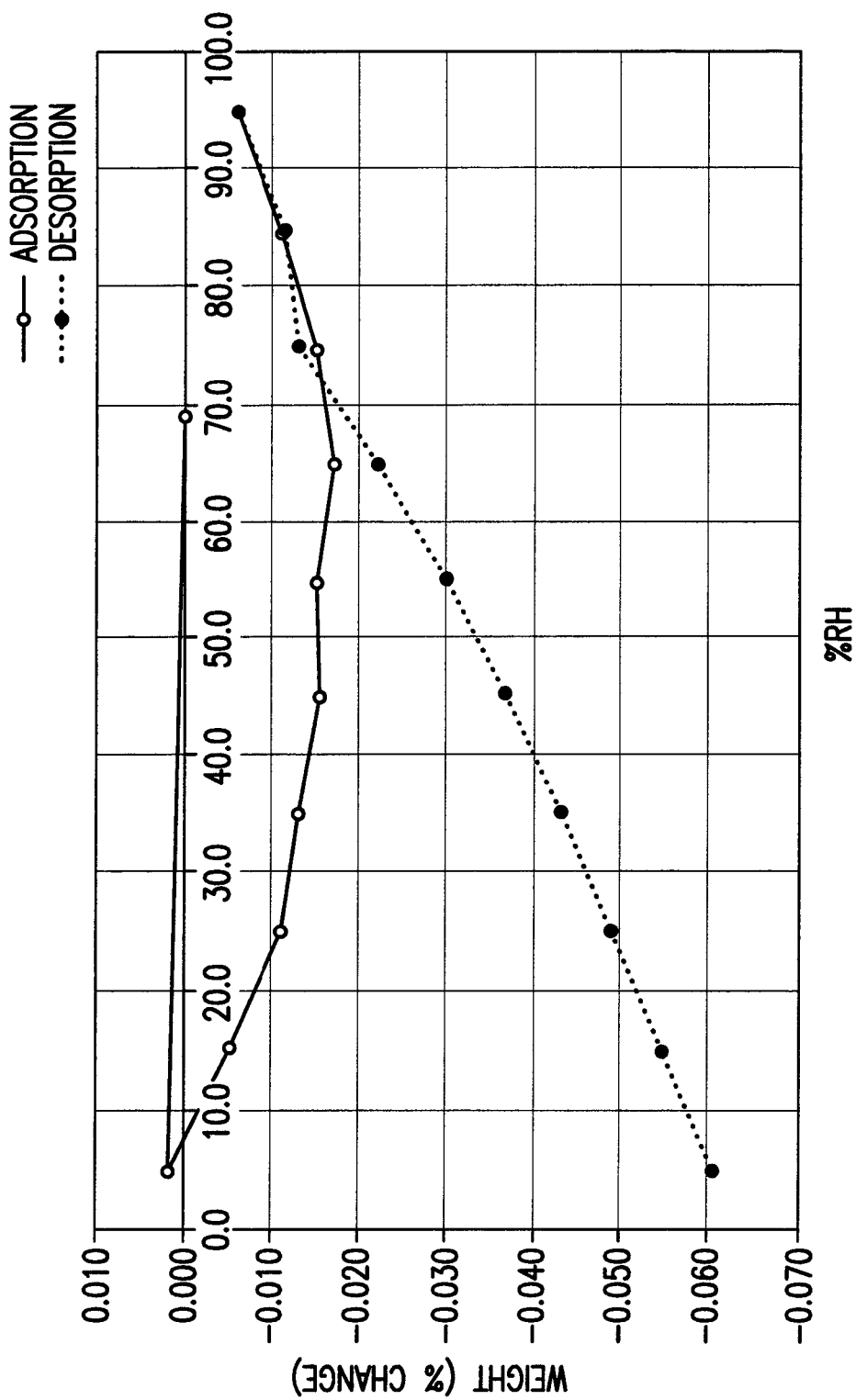

FIG. 7 provides a DVS isotherm of a sample comprising Form B of 3-[5-(2-fluorophenyl)-[1,2,4]oxadiazol-3-yl]-benzoic acid.

Figure 8:
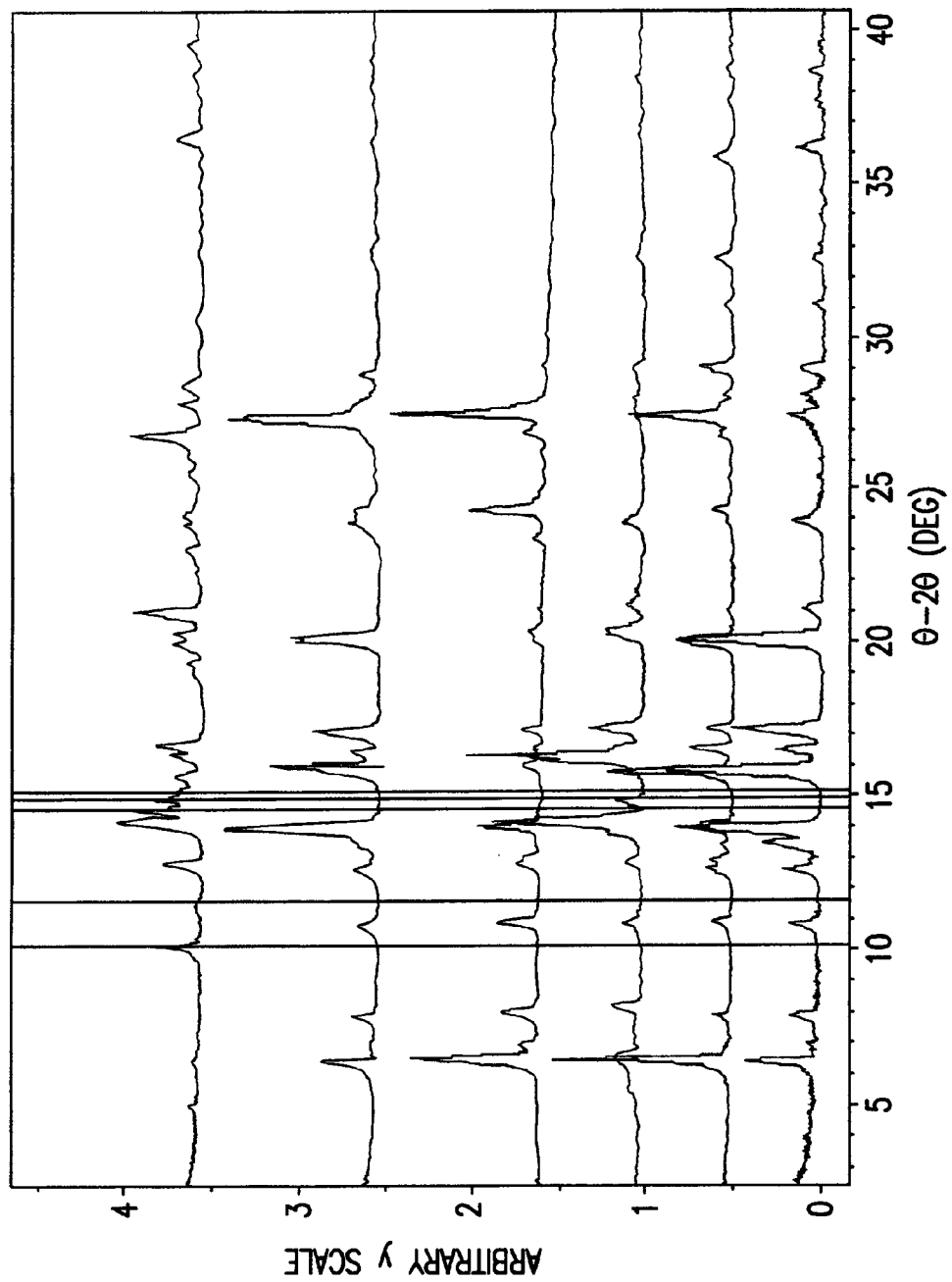

FIG. 8 provides an overlay of experimental XRPD patterns showing a characteristic peak set of Form A (Top) with respect to several samples comprising Form B (second from top to bottom) of 3-[5-(2-fluorophenyl)-[1,2,4]oxadiazol-3-yl]-benzoic acid, illustrating peak shift among certain Form B samples.

Figure 9:
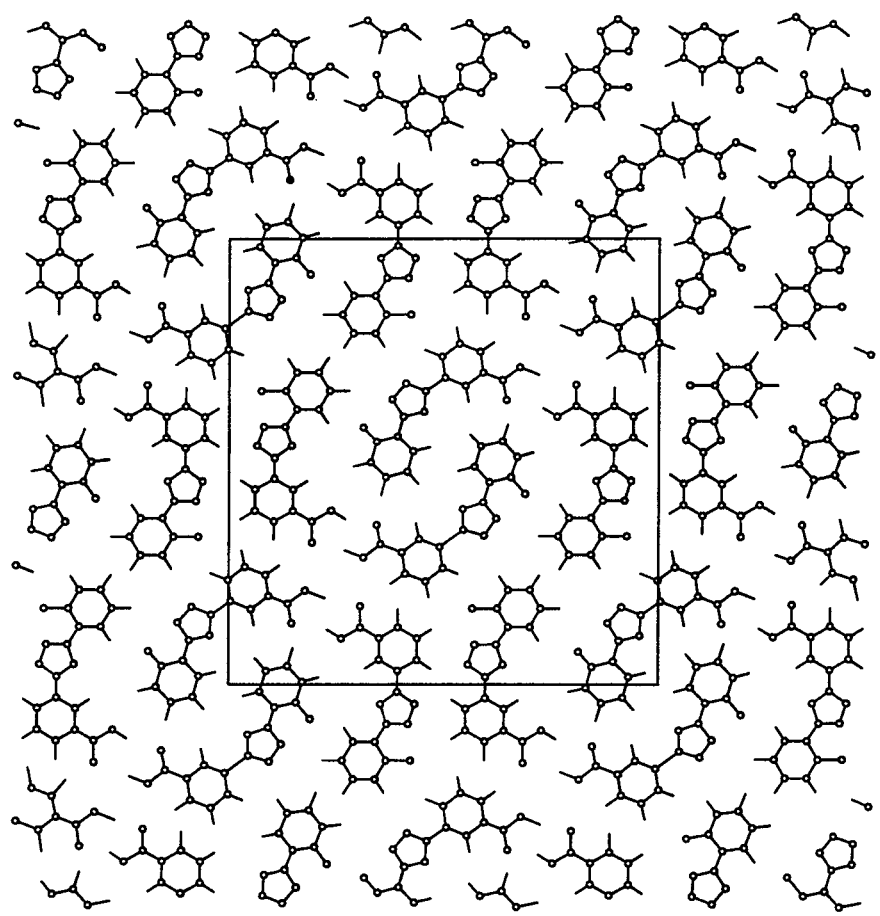

FIG. 9 provides crystal packing diagram of Form A of 3-[5-(2-fluorophenyl)-[1,2,4]oxadiazol-3-yl]-benzoic acid, viewed down the crystallographic b axis and showing an outline of the unit cell.

Figure 10:
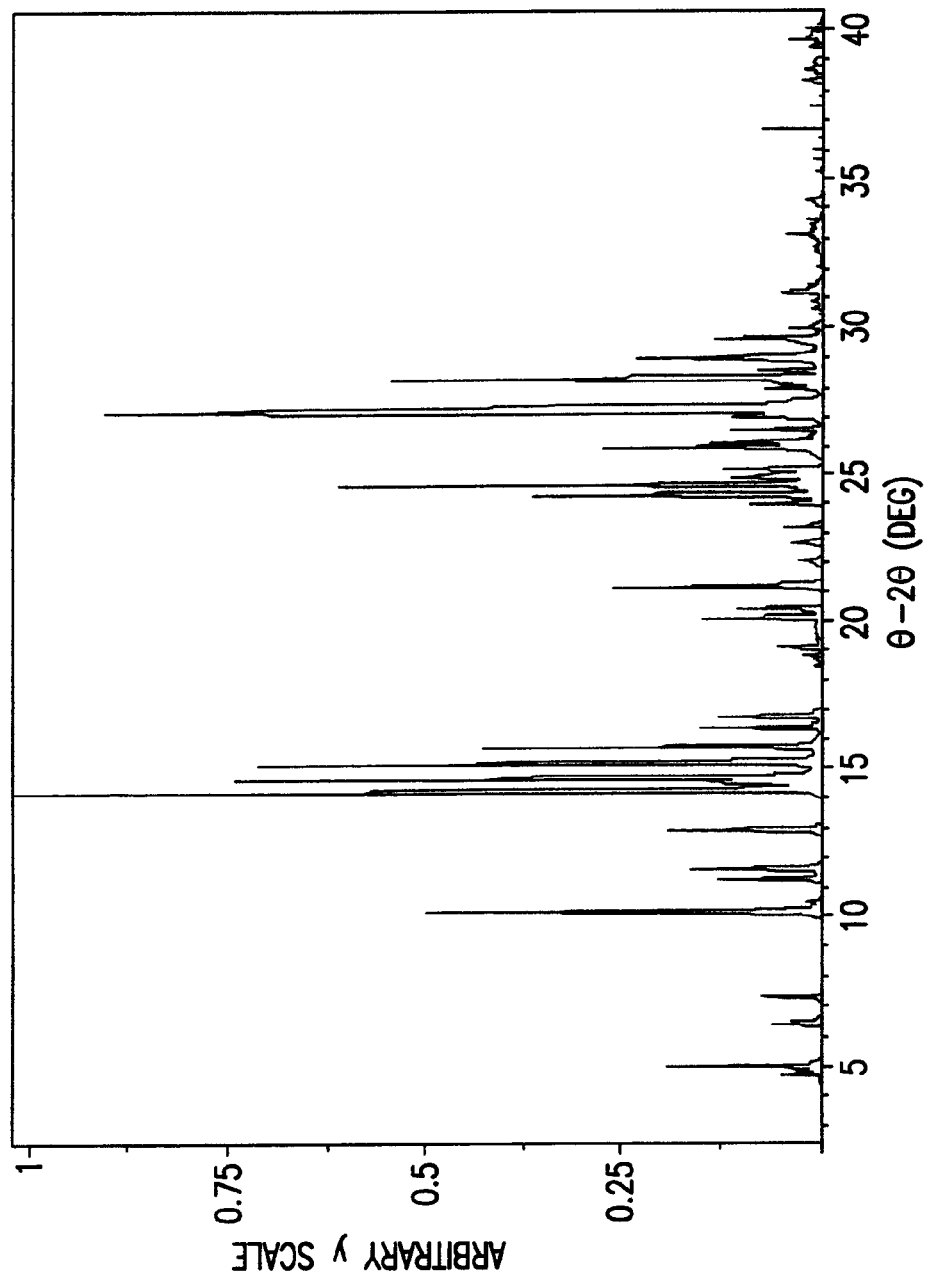

FIG. 10 provides a XRPD pattern of Form A of 3-[5-(2-fluorophenyl)-[1,2,4]oxadiazol-3-yl]-benzoic acid simulated from a single-crystal X-ray diffraction crystal structure obtained from a representative single crystal of Form A.

Figure 11:
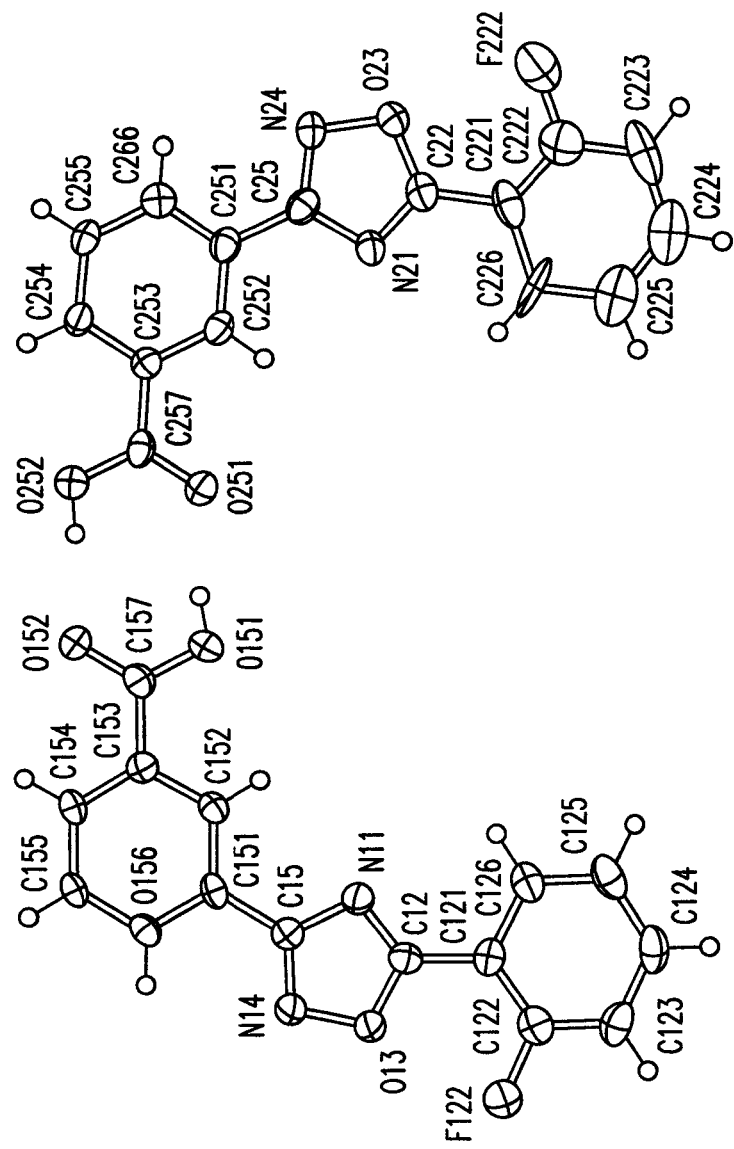

FIG. 11 provides a ORTEP plot of the asymmetric unit of the single-crystal XRD crystal structure of Form A of 3-[5-(2-fluorophenyl)-[1,2,4]oxadiazol-3-yl]-benzoic acid. Atoms are represented by 50% probability anisotropic thermal ellipsoids.

4.2 TERMINOLOGY

Crystalline forms equivalent to the crystalline forms described below and claimed herein may demonstrate similar, yet non-identical, analytical characteristics within a reasonable range of error, depending on test conditions, purity, equipment and other common variables known to those skilled in the art or reported in the literature. The term "crystalline" and related terms used herein, when used to describe a substance, component or product, means that the substance, component or product is substantially crystalline as determined by X-ray diffraction, microscopy, polarized microscopy, or other known analytical procedure known to those skilled in the art. See, e.g., Remington's Pharmaceutical Sciences, 18th ed., Mack Publishing, Easton Pa., 173 (1990); *The United States Pharmacopeia*, 23rd ed., 1843-1844 (1995).

Accordingly, it will be apparent to those skilled in the art that various modifications and variations can be made in the present invention without departing from the scope and spirit of the invention. Other embodiments of the invention will be apparent to those skilled in the art from consideration of the specification and practice of the invention disclosed herein. Applicants intend that the specification and examples be considered as exemplary, but not limiting in scope.

The crystalline forms of the instant invention can be characterized using Single Crystal Data, Powder X-Ray Diffraction (PXRD), Differential Scanning calorimetry (DSC), and Thermogravimetric Analysis (TGA). It is to be understood that numerical values described and claimed herein are approximate. Variation within the values may be attributed to equipment calibration, equipment errors, purity of the materials, crystals size, and sample size, among other factors. In addition, variation may be possible while still obtaining the same result. For example, X-ray diffraction values are generally accurate to within .+−.0.2 degrees and intensities (including relative intensities) in an X-ray diffraction pattern may fluctuate depending upon measurement conditions employed. Similarly, DSC results are typically accurate to within about 2° C. Consequently, it is to be understood that the crystalline forms of the instant invention are not limited to the crystalline forms that provide characterization patterns (i.e., one or more of the PXRD, DSC, and TGA) completely identical to the characterization patterns depicted in the accompanying Figures disclosed herein. Any crystalline forms that provide characterization patterns substantially the same as those described in the accompanying Figures fall within the scope of the present invention. The ability to ascertain substantially the same characterization patterns is within the purview of one of ordinary skill in the art.

The embodiments provided herein can be understood more fully by reference to the following detailed description and illustrative examples, which are intended to exemplify non-limiting embodiments.

Processes for the preparation of 3-[5-(2-fluorophenyl)-[1,2,4]oxadiazol-3-yl]-benzoic acid are described in U.S. Pat. No. 6,992,096 B2, issued Jan. 31, 2006, and U.S. patent application Ser. No. 11/899,813, filed Sep. 9, 2007, both of which are incorporated by reference in their entirety.

4.3 Form A of 3-[5-(2-fluorophenyl)-[1,2,4]oxadiazol-3-yl]-benzoic acid

In one embodiment, the present invention provides the Form A crystal form of 3-[5-(2-fluorophenyl)-[1,2,4]oxadiazol-3-yl]-benzoic acid. In certain embodiments, Form A can be obtained by crystallization from various solvents, including, but not limited to, methanol, tertiary-butyl alcohol (t-BuOH), 1-butyl alcohol (1-BuOH), acetonitrile, isopropyl alcohol (IPA), isopropyl ether, dimethyl formamide, heptane, isopropyl acetate (IPOAc), toluene and/or water. A representative XRPD pattern of Form A of 3-[5-(2-fluorophenyl)-[1,2,4]oxadiazol-3-yl]-benzoic acid is provided in FIG. 1. In certain embodiments, Form A of 3-[5-(2-fluorophenyl)-[1,2,4]oxadiazol-3-yl]-benzoic acid has an XRPD pattern which is substantially similar to the pattern displayed in FIG. 1.

Representative thermal characteristics of Form A of 3-[5-(2-fluorophenyl)-[1,2,4]oxadiazol-3-yl]-benzoic acid are shown in FIG. 2. A representative DSC thermogram, presented in FIG. 2, exhibits an endothermic event with a peak temperature at about 244° C. A representative TGA thermogram, also presented in FIG. 2, exhibits a mass loss of less than about 1% of the total mass of the sample upon heating from about 33° C. to about 205° C. These thermal data indicate that Form A of 3-[5-(2-fluorophenyl)-[1,2,4]oxadiazol-3-yl]-benzoic acid does not contain substantial amounts of either water or solvent in the crystal lattice. In certain embodiments, Form A exhibits a TGA weight loss event commencing at about 212° C. which corresponds to sublimation prior to melting.

A single-crystal X-ray diffraction (XRD) crystal structure was obtained from a representative single crystal of Form A of 3-[5-(2-fluorophenyl)-[1,2,4]oxadiazol-3-yl]-benzoic acid. Using XRD data collected at about 150 K, the following unit cell parameters were obtained: a=24.2240(10) Å; b=3.74640(10) Å; c=27.4678(13) Å; α=90°; β=92.9938(15)°; γ=90'; V=2489.38(17) Å$^3$. A crystal packing diagram from the single-crystal XRD structure of Form A, viewed down the crystallographic b axis, is provided as FIG. 9. A simulated XRPD pattern was generated for Cu radiation using Powder-Cell 2.3 (PowderCell for Windows Version 2.3 Kraus, W.; Nolze, G. Federal Institute for Materials Research and Testing, Berlin Germany, EU, 1999) and the atomic coordinates, space group, and unit cell parameters from the single crystal data. A simulated XRPD pattern of Form A of 3-[5-(2-fluorophenyl)-[1,2,4]oxadiazol-3-yl]-benzoic acid is provided as FIG. 10.

In certain embodiments, Form A of 3-[5-(2-fluorophenyl)-[1,2,4]oxadiazol-3-yl]-benzoic acid is characterized by its physical stability when subjected to certain processing conditions. In certain embodiments, Form A is physically stable when stored for 6 days at one or more of the following relative humidity (RH) conditions: 53% RH at 40° C.; 75% RH at 40° C.; 50% RH at 60° C.; and 79% RH at 60° C. In other embodiments, Form A is physically stable when milled at ambient and at sub-ambient temperatures. In other embodiments, Form A is physically stable when slurried at one or more of the following conditions: in 1-BuOH for 4 days at ambient temperature; in chloroform for 2 days at 50° C.; and in dichloromethane for 2 days at 50° C.

Form A of 3-[5-(2-fluorophenyl)-[1,2,4]oxadiazol-3-yl]-benzoic acid was evaluated for hygroscopicity. Dynamic vapor sorption (DVS) analysis of moisture uptake and moisture release as a function of relative humidity (RH) were obtained upon cycling between 5% and 95% RH. The maximum uptake was about 0.06% of the total mass of the sample, as demonstrated in the representative Form A DVS isotherm in FIG. 3. Accordingly, in certain embodiments, Form A is non-hygroscopic.

A representative $^{13}$C solid-state NMR spectrum of 3-[5-(2-fluorophenyl)-[1,2,4]oxadiazol-3-yl]-benzoic acid is provided in FIG. 4. In certain embodiments, Form A of 3-[5-(2-fluorophenyl)-[1,2,4]oxadiazol-3-yl]-benzoic acid is characterized by $^{13}$C CP/MAS solid-state NMR signals located at one or more of the following approximate positions: 172.6, 167.0, 131.3, 128.4; and 117.1 ppm, when externally referenced to glycine at 176.5 ppm.

In certain embodiments, Form A of 3-[5-(2-fluorophenyl)-[1,2,4]oxadiazol-3-yl]-benzoic acid exhibits desirable characteristics for the processing and/or manufacture of drug product containing 3-[5-(2-fluorophenyl)-[1,2,4]oxadiazol-3-yl]-benzoic acid. For example, in certain embodiments, Form A of 3-[5-(2-fluorophenyl)-[1,2,4]oxadiazol-3-yl]-benzoic acid has a relatively high melting point, which is an important characteristic for, inter alia, processing and manufacturing. Moreover, in certain embodiments, Form A of 3-[5-(2-fluorophenyl)-[1,2,4]oxadiazol-3-yl]-benzoic acid was found to be substantially non-hygroscopic. A non-hygroscopic solid form is desirable for a variety of reasons including, for example, for processing and storage concerns. Moreover, in certain embodiments, Form A of 3-[5-(2-fluorophenyl)-[1,2,4]oxadiazol-3-yl]-benzoic acid was found to be physically and chemically stable upon micronization, a method of particle size reduction. Physical stability is an important property of pharmaceutical materials during manufacture, processing, and storage.

4.4 Form B of 3-[5-(2-fluorophenyl)-[1,2,4]oxadiazol-3-yl]-benzoic acid

In one embodiment, the present invention provides the Form B crystal form of 3-[5-(2-fluorophenyl)-[1,2,4]oxadiazol-3-yl]-benzoic acid. In certain embodiments, Form B can be obtained by crystallization from various solvents, including, but not limited to, tetrahydrofuran (THF), hexane, isopropyl alcohol (IPA) ethyl acetate (EtOAc), acetic acid, 1-butyl acetate, acetone, dimethyl ether, diethyl ether, dioxane, water, methyl isobutyl ketone (MIBK), methyl ethyl ketone (MEK), nitromethane and or water.

In certain embodiments of the invention, Form B of 3-[5-(2-fluorophenyl)-[1,2,4]oxadiazol-3-yl]-benzoic acid has solvent in the crystal lattice in an amount which depends upon one or more conditions such as, but not limited to, crystallization, treatment, processing, formulation, manufacturing or storage. In certain embodiments of the invention, Form B has solvent in the crystal lattice. In certain embodiments, Form B is essentially free of solvent in the crystal lattice. In certain embodiments, the maximum combined molar equivalents of solvent per mole of 3-[5-(2-fluorophenyl)-[1,2,4]oxadiazol-3-yl]-benzoic acid in a sample of Form B is less than 6, less than 5, less than 4, less than 3, less than 2, less than 1.5, less than 1, less than 0.75, less than 0.5, or less than 0.25 molar equivalents. Without intending to be limited by theory, it is believed that the characteristic variably in the solvent content of Form B arises from the existence of a lattice channel which can accommodate different types and/or amounts of solvent, and which permits the addition and/or removal of solvents depending upon the particular conditions. In certain embodiments, the structure of Form B represents the basis for an isostructural family of crystal forms. In certain embodiments, Form B is a desolvated solvate crystal form.

A representative XRPD pattern of Form B of 3-[5-(2-fluorophenyl)-[1,2,4]oxadiazol-3-yl]-benzoic acid is provided in FIG. 5. In certain embodiments, Form A of 3-[5-(2-fluorophenyl)-[1,2,4]oxadiazol-3-yl]-benzoic acid is characterized by XRPD peaks located at one or more of the following positions: about 6.4, about 8.0, about 14.1, about 15.9, about 17.2 and about 20.1 degrees 2θ. It is understood by one of skill in the art that when solvents and/or water are added or removed from a crystal lattice, the lattice will slightly expands or contract, resulting in minor shifts in the position of XRPD peaks. In certain embodiments of the present invention, Form B of 3-[5-(2-fluorophenyl)-[1,2,4]oxadiazol-3-yl]-benzoic acid is provided which is characterized by an XRPD pattern substantially similar to the pattern displayed in FIG. 5. In certain embodiments, Form B exhibits a XRPD pattern substantially similar to the pattern displayed in FIG. 5 but exhibits small shifts in peak positions resulting from the presence or absence of specific solvents or water in the crystal lattice. Certain representative XRPD patterns of Form B (second from top to bottom) are compared to Form A (top) of 3-[5-(2-fluorophenyl)-[1,2,4]oxadiazol-3-yl]-benzoic acid in FIG. 8. In certain embodiments, Form B has a XRPD pattern substantially similar to one or more of the XRPD patterns displayed in FIG. 8.

Thermal characteristics of a sample of Form B of 3-[5-(2-fluorophenyl)-[1,2,4]oxadiazol-3-yl]-benzoic acid crystallized from a 2.5:1 THF:hexane mixture are shown in FIG. 6. A TGA thermogram of this Form B sample, presented in FIG. 6, exhibits two mass loss events: one mass loss event of about 5% of the total mass of the sample upon heating from about 25° C. to about 165° C., and a second mass loss event commencing at about 220° C. Hotstage microscopy revealed that the first mass loss event resulted from the loss of solvent and/or water from the crystal lattice, and the second mass loss event resulted from the sublimation of Form B. XRPD analysis of the resulting sublimate indicated that Form A of 3-[5-(2-fluorophenyl)-[1,2,4]oxadiazol-3-yl]-benzoic acid had formed. A DSC thermogram of this Form B sample, presented in FIG. 6, exhibits a sharp endothermic event with a peak temperature at about 243° C., corresponding to the melt of the Form A sublimate. The DSC of this Form B sample also exhibits at least one other event at a temperature below about 220° C. These thermal data indicate that this sample of Form B of 3-[5-(2-fluorophenyl)-[1,2,4]oxadiazol-3-yl]-benzoic acid contained water and/or solvent in the crystal lattice. On account of the variable water and/or solvent content of certain samples of Form B of 3-[5-(2-fluorophenyl)-[1,2,4]oxadiazol-3-yl]-benzoic acid, in certain embodiments of the invention the thermal characteristics of Form B will exhibit certain variation. For example, in specific embodiments of the invention, samples of Form B which are essentially free of water and solvent do not exhibit a substantial TGA mass loss or DSC thermal event below about 220° C. Because Form B sublimes and crystallizes as Form A, thus in FIG. 6, the heat of fusion for the endotherm is after the sample has converted to Form A.

In one embodiment of the invention, a Form B sample which crystallized from IPA had about 0.1 molar equivalents of IPA and about 1 molar equivalents of water per mole of 3-[5-(2-fluorophenyl)-[1,2,4]oxadiazol-3-yl]-benzoic acid, based upon analysis using TGA and $^1$H NMR. In specific embodiments of the invention, a Form B sample which possesses approximately 1 molar equivalent of water per molar equivalent of 3-[5-(2-fluorophenyl)-[1,2,4]oxadiazol-3-yl]-benzoic acid is termed a monohydrate. In another embodiment of the invention, a Form B sample which was treated by vacuum drying at 105° C. for 10 min exhibited a total weight loss of 2% of the mass of the sample when subsequently analyzed by TGA from about 25 to about 185° C. In certain embodiments, the Form B characteristics which are dependent upon the quantity and/or identity of the solvent and/or water in the crystal lattice (e.g., mass loss upon heating or drying) will exhibit variation with respect to the total quantity or identity of solvent and/or water in the crystal lattice. In certain embodiments, regardless of the quantity and/or identity of solvent and/or water in the crystal lattice, the XRPD pattern of Form B will exhibit peaks characteristic of Form B as described supra, but with minor peak shifting arising from differences in quantity and/or identity of the solvent and/or water in the Form B crystal lattice. Representative XRPD patterns illustrating peak shifting among certain Form B samples are overlaid in FIG. 8 (second from top to bottom).

In certain embodiments of the invention, upon milling at ambient or sub-ambient temperatures, conversion from Form B to Form A is observed. In other embodiments of the invention, Form B is physically stable upon storage for 6 days at one of the following relative humidity (RH) conditions: 53% RH at 40° C.; 75% RH at 40° C.; and 50% RH at 60° C. In other embodiments of the invention, Form B is substantially non-hygroscopic, as illustrated by the representative Form B DVS isotherm in FIG. 7. In other embodiments of the invention, Form B exhibited partial conversion to Form A upon storage for 6 days at the condition of 79% RH at 60° C. In other embodiments of the invention, Form B is physically stable under compression alone and under compression in the presence of a 1:1 mixture of t-BuOH and water. In other embodiments of the invention, Form B is physically stable when slurried for 1 day at ambient temperature in a 1:1 mixture of THF and heptane. In other embodiments, conversion of Form B to Form A is observed upon slurrying Form B in either methyl isobutyl ketone or a 1:1 mixture of dioxane and water.

4.5 Methods of Use

Provided herein are methods of treating, preventing and managing diseases or disorders ameliorated by the suppression of premature translation termination and/or nonsense-mediated mRNA decay in a patient which comprise administering to a patient in need thereof an effective amount of a solid form of 3-[5-(2-fluoro-phenyl)-[1,2,4]oxadiazol-3-yl]-benzoic acid.

In one embodiment, provided herein are methods for the treatment, prevention or management of any disease that is associated with a gene exhibiting premature translation termination and/or nonsense-mediated mRNA decay. In one embodiment, the disease is due, in part, to the lack of expression of the gene resulting from a premature stop codon. Specific examples of genes which may exhibit premature translation termination and/or nonsense-mediated mRNA decay and diseases associated with premature translation termination and/or nonsense-mediated mRNA decay are found in U.S. Patent Application Publication No. 2005-0233327, titled: Methods For Identifying Small Molecules That Modulate Premature Translation Termination And Nonsense Mediated mRNA Decay, which is incorporated herein by reference in its entirety.

Diseases or disorders associated with or ameliorated by the suppression of premature translation termination and/or nonsense-mediated mRNA decay include, but are not limited to: a genetic disease, cancer, an autoimmune disease, a blood disease, a collagen disease, diabetes, a neurodegenerative disease, a proliferative disease, a cardiovascular disease, a pulmonary disease, an inflammatory disease or central nervous system disease.

Specific genetic diseases within the scope of the methods of the invention include, but are not limited to, multiple endocrine neoplasia (type 1, 2 and 3), amyloidosis, mucopolysaccharidosis (type I and III), congenital adrenal hypoplasia, adenomatous poliposis coli, Von Hippel Landau Disease, Menkes Syndrome, hemophilia A, hemophilia B, collagen VII, Alagille Syndrome, Townes-Brocks Syndrome, rhabdoid tumor, epidermolysis bullosa, Hurler's Syndrome, Coffin-Lowry Syndrome, aniridia, Charcot-Maria-Tooth Disease, myotubular myopathy, X-linked myotubular myopathy, X-linked chondrodysplasia, X-linked agammaglobulinemia, polycystic kidney disease, spinal muscular atrophy, familial adenomatous poliposis, pyruvate dehydrogenase deficiency, phenylketonuria, neurofibromatosis 1, neurofibromatosis 2, Alzheimer's disease, Tay Sachs disease, Rett Syndrome, Hermansky-Pudlak Syndrome, ectodermal dysplasia/skin fragility syndrome, Leri-Weill dyschondrosteosis, rickets, hypophosphataemic, adrenoleukodystrophy, gyrate atrophy, atherosclerosis, sensorineural deafness, dystonia, Dent Disease, acute intermittent porphyria, Cowden Disease, Herlitz epidermolysis bullosa, Wilson Disease, Treacher-Collins Syndrome, pyruvate kinase deficiency, giantism, dwarfism, hypothyroidism, hyperthyroidism, aging, obesity, Parkinson's disease, Niemann Pick's disease C, Cystic Fibrosis, muscular dystrophy, heart disease, kidney stones, ataxia-telangiectasia, familial hypercholesterolemia, retinitis pigmentosa, lysosomal storage disease, tuberous sclerosis, Duchenne Muscular Dystrophy, and Marfan Syndrome.

In another embodiment, the genetic disease is an autoimmune disease. In a preferred embodiment, the autoimmune disease is rheumatoid arthritis or graft versus host disease.

In another embodiment, the genetic disease is a blood disease. In a particular embodiment, the blood disease is hemophilia A, Von Willebrand disease (type 3), ataxia-telangiectasia, b-thalassemia or kidney stones.

In another embodiment, the genetic disease is a collagen disease. In a particular embodiment, the collagen disease is osteogenesis imperfecta or cirrhosis.

In another embodiment, the genetic disease is diabetes.

In another embodiment, the genetic disease is an inflammatory disease. In a particular embodiment, the inflammatory disease is arthritis.

In another embodiment, the genetic disease is a central nervous system disease. In one embodiment the central nervous system disease is a neurodegenerative disease. In a particular embodiment, the central nervous system disease is multiple sclerosis, muscular dystrophy, Duchenne muscular dystrophy, Alzheimer's disease, Tay Sachs disease, late infantile neuronal ceroid lipofuscinosis (LINCL) or Parkinson's disease.

In another embodiment, the genetic disease is cancer. In a particular embodiment, the cancer is of the head and neck, eye, skin, mouth, throat, esophagus, chest, bone, lung, colon, sigmoid, rectum, stomach, prostate, breast, ovaries, kidney, liver, pancreas, brain, intestine, heart or adrenals. The cancer can be primary or metastatic. Cancers include solid tumors, hematological cancers and other neoplasias.

In another particular embodiment, the cancer is associated with tumor suppressor genes (see e.g. Garinis et al. 2002, Hum Gen 111:115-117; Meyers et al. 1998, Proc. Natl. Acad. Sci. USA, 95: 15587-15591; Kung et al. 2000, Nature Medicine 6(12): 1335-1340. Such tumor suppressor genes include, but are not limited to, APC, ATM, BRAC1, BRAC2, MSH1, pTEN, Rb, CDKN2, NF1, NF2, WT1, and p53.

In a particularly preferred embodiment, the tumor suppressor gene is the p53 gene. Nonsense mutations have been identified in the p53 gene and have been implicated in cancer. Several nonsense mutations in the p53 gene have been identified (see, e.g., Masuda et al., 2000, Tokai J Exp Clin Med. 25(2):69-77; Oh et al., 2000, Mol Cells 10(3):275-80; Li et al., 2000, Lab Invest. 80(4):493-9; Yang et al., 1999, Zhonghua Zhong Liu Za Zhi 21(2):114-8; Finkelstein et al., 1998, Mol Diagn. 3(1):37-41; Kajiyama et al., 1998, Dis Esophagus. 11(4):279-83; Kawamura et al., 1999, Leuk Res. 23(2): 115-26; Radig et al., 1998, Hum Pathol. 29(11):1310-6; Schuyer et al., 1998, Int J Cancer 76(3):299-303; Wang-Gohrke et al., 1998, Oncol Rep. 5(1):65-8; Fulop et al., 1998, J Reprod Med. 43(2):119-27; Ninomiya et al., 1997, J Dermatol Sci. 14(3):173-8; Hsieh et al., 1996, Cancer Lett. 100 (1-2):107-13; Rall et al., 1996, Pancreas. 12(1):10-7; Fukutomi et al., 1995, Nippon Rinsho. 53(11):2764-8; Frebourg et al., 1995, Am J Hum Genet. 56(3):608-15; Dove et al., 1995, Cancer Surv. 25:335-55; Adamson et al., 1995, Br J. Haematol. 89(1):61-6; Grayson et al., 1994, Am J Pediatr Hematol Oncol. 16(4):341-7; Lepelley et al., 1994, Leukemia. 8(8): 1342-9; McIntyre et al., 1994, J Clin Oncol. 12(5):925-30; Horio et al., 1994, Oncogene. 9(4):1231-5; Nakamura et al., 1992, Jpn J Cancer Res. 83(12):1293-8; Davidoff et al., 1992, Oncogene. 7(1):127-33; and Ishioka et al., 1991, Biochem Biophys Res Commun. 177(3):901-6; the disclosures of which are hereby incorporated by reference in their entireties).

In other embodiments, diseases to be treated, prevented or managed by administering to a patient in need thereof an effective amount of a solid form of 3-[5-(2-fluoro-phenyl)-[1,2,4]oxadiazol-3-yl]-benzoic acid include, but are not limited to, solid tumor, sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma, retinoblastoma, a blood-born tumor, acute lymphoblastic leukemia, acute lymphoblastic B-cell leukemia, acute lymphoblastic T-cell leukemia, acute myeloblastic leukemia, acute promyelocytic leukemia, acute monoblastic leukemia, acute erythroleukemic leukemia, acute megakaryoblastic leukemia, acute myelomonocytic leukemia, acute nonlymphocycitc leukemia, acute undifferentiated leukemia, chronic myelocytic leukemia, chronic lymphocytic leukemia, hairy cell leukemia, or multiple myeloma. See e.g., *Harrison's Principles of Internal Medicine*, Eugene Braunwald et al., eds., pp. 491-762 (15th ed. 2001).

4.6 Pharmaceutical Compositions

Pharmaceutical compositions and single unit dosage forms comprising a compound of the invention, or a pharmaceutically acceptable polymorph, prodrug, salt, solvate, hydrate, or clathrate thereof, are also encompassed by the invention. Individual dosage forms of the invention may be suitable for oral, mucosal (including sublingual, buccal, rectal, nasal, or vaginal), parenteral (including subcutaneous, intramuscular, bolus injection, intraarterial, or intravenous), transdermal, or topical administration.

Single unit dosage forms of the invention are suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient.

The composition, shape, and type of dosage forms of the invention will typically vary depending on their use. These and other ways in which specific dosage forms encompassed by this invention will vary from one another will be readily apparent to those skilled in the art. See, e.g., *Remington's Pharmaceutical Sciences*, 18th ed., Mack Publishing, Easton Pa. (1995).

Typical pharmaceutical compositions and dosage forms comprise one or more carriers, excipients or diluents. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form.

5. EXAMPLES

5.1 Synthesis of solid forms of the of 3-[5-(2-fluorophenyl)-[1,2,4]oxadiazol-3-yl]-benzoic acid The 3-[5-(2-fluorophenyl)-[1,2,4]oxadiazol-3-yl]-benzoic acid product obtained from the synthesis described supra may be crystallized or recrystallized in a number of ways to yield the solid forms of the invention. Provided below are several non-limiting examples.

5.1.1 Synthesis of Form A

5.1.1.1 Slow Evaporation

The 3-[5-(2-fluorophenyl)-[1,2,4]oxadiazol-3-yl]-benzoic acid product obtained as described herein was crystallized as Form A by the method of slow evaporation from the each one of the following solvents: acetonitrile; t-butanol; isopropyl alcohol; and isopropyl ether. A solution of 3-[5-(2-fluorophenyl)-[1,2,4]oxadiazol-3-yl]-benzoic acid was prepared in the indicated solvent and sonicated between aliquot additions to assist in dissolution. Once a mixture reached complete dissolution, as judged by visual observation, the solution was filtered through a 0.2-μm filter. The filtered solution was allowed to evaporate at a temperature of 60° C. (50° C. in the case of t-butanol), in a vial covered with aluminum foil containing pinhole(s). The solids that formed were isolated and characterized by XRPD as Form A.

5.1.1.2 Fast Evaporation

The 3-[5-(2-fluorophenyl)-[1,2,4]oxadiazol-3-yl]-benzoic acid product obtained as described herein was crystallized as Form A by the method of fast evaporation from each one of the following solvents or solvent systems: 1-butanol; dimethoxyether; t-butanol; a mixture of dimethyl formamide and water; isopropyl ether; and a mixture of t-butanol:water (in a 3:2 ratio), 1 molar equivalent methanol and 1 molar equivalent sodium chloride. Solutions were prepared in the indicated solvent or solvent system and sonicated between aliquot additions to assist in dissolution. Once a mixture reached complete dissolution, as judged by visual observation, the solution was filtered through a 0.2-μm filter. The filtered solution was allowed to evaporate at a temperature of 60° C. (50° C. in the cases of t-butanol and isopropyl ether; 81° C. in the case of the t-butanol/water/methanol/NaCl system) in an open vial. The solids that formed were isolated and characterized by XRPD as Form A.

5.1.1.3 Slurry Conversion

Form B of the free acid of 3-[5-(2-fluorophenyl)-[1,2,4]oxadiazol-3-yl]-benzoic acid, obtained as described herein, was converted to Form A by the method of slurrying in the solvent system 1:1 dioxane:water. A slurry was prepared by adding enough Form B solids to a given solvent so that excess solids were present. The mixture was then agitated in a sealed vial at a temperature of 60° C. After 2 days, the solids were isolated by vacuum filtration and characterized by XRPD as Form A with a minor amount of Form B.

5.1.1.4 Sublimation and Heating

Form B of 3-[5-(2-fluorophenyl)-[1,2,4]oxadiazol-3-yl]-benzoic acid, obtained as described herein, was converted to Form A by the methods of sublimation and heating. In one experiment, Form B was sublimed at 160-208° C., under vacuum, for 35 minutes to yield white needles which were characterized by XRPD as Form A. In another experiment, Form B was melted at 255° C., followed by direct placement into liquid nitrogen to yield crystalline material which was characterized by XRPD as Form A. In another experiment, Form B was melted at 255° C. and then cooled slowly to yield crystalline material which was characterized by XRPD as Form A.

5.1.2 Synthesis of Form B

5.1.2.1 Slow Evaporation

The 3-[5-(2-fluorophenyl)-[1,2,4]oxadiazol-3-yl]-benzoic acid product obtained as described herein was crystallized as Form B by the method of slow evaporation from each one of the following solvents: acetone; dimethyl ether; and methyl ethyl ketone. A solution of 3-[5-(2-fluorophenyl)-[1,2,4]oxadiazol-3-yl]-benzoic acid was prepared in the indicated solvent and sonicated between aliquot additions to assist in dissolution. Once a mixture reached complete dissolution, as judged by visual observation, the solution was filtered through a 0.2-μm filter. The filtered solution was allowed to evaporate at a temperature of 50° C. (60° C. in the case of methyl ethyl ketone), in a vial covered with aluminum foil containing pinhole(s).

In one embodiment, 3-[5-(2-fluorophenyl)-[1,2,4]oxadiazol-3-yl]-benzoic acid was dissolved in dimethoxyether. The solution was into a clean vial. The vial was filtered through a 0.2-μm filter covered with aluminum foil perforated with pinhole(s) and the solvent allowed to evaporate. The solids that formed were isolated and characterized by XRPD as Form B. XRPD analysis is illustrated in Table 8 (P.O.)

5.1.2.2 Fast Evaporation

The 3-[5-(2-fluorophenyl)-[1,2,4]oxadiazol-3-yl]-benzoic acid product obtained as described herein was crystallized as Form B by the method of fast evaporation from each one of the following solvents or solvent systems: acetone, acetic acid, 1-butyl acetate; dimethyl ether; THF and diethyl ether; dioxane; methyl ethyl ketone; nitromethane; methyl iso-butyl ketone; THF:hexane (2.5:1); and dioxane:water (3:2). Solutions were prepared in the indicated solvent or solvent system and sonicated between aliquot additions to assist in dissolution. Once a mixture reached complete dissolution, as judged by visual observation, the solution was filtered through a 0.2-μm filter. The filtered solution was allowed to evaporate at an elevated temperature in an open vial. The solids that formed were isolated and characterized by XRPD as Form B.

5.1.2.3 Slurry Conversion

Form A of 3-[5-(2-fluorophenyl)-[1,2,4]oxadiazol-3-yl]-benzoic acid, obtained as described herein, was converted to Form B by the method of slurrying in each one of the following solvents: acetic acid; 1-butyl acetate; and nitromethane. In one embodiment, 3-[5-(2-fluorophenyl)-[1,2,4]oxadiazol-3-yl]-benzoic acid was slurried on an orbit shaker in 1-butyl acetate (13 mL) at room temperature for 3 days. After three days the solvent was removed by pipette, dried and characterized by XRPD as Form B (Table 5)

5.1.2.4 Orbit Shaker Conversion

Form A of 3-[5-(2-fluorophenyl)-[1,2,4]oxadiazol-3-yl]-benzoic acid, obtained as described herein, was converted to Form B by heating on an orbit shaker in 1-propanol (10 mL) at 60° C. for 1 day on an orbit shaker. The resulting solution was through 0.2 μm nylon filter into a clean vial. After 1 day, the solvent was decanted and the sample dried under nitrogen. XRPD analysis as form B is illustrated in Table 4.

5.1.2.5 Other Embodiments

3-[5-(2-fluorophenyl)-[1,2,4]oxadiazol-3-yl]-benzoic acid (20 mg, Form B) was slurried in a mixture of tetrahydrofuran/heptane 1/1 (2 mL) at ambient temperature for 1 day. After 1 day, the slurry was seeded with Form A (10 mg) and Form B (9 mg) and slurried for an additional day, after which time additional Form A (30 mg) was added. After slurrying the sample a total of 7 days additional Form A was added (30 mg) and the temperature increased to 50° C. Solids were collected after slurrying at 50° C. for one day. The solids that formed were isolated and characterized by XRPD as Form B. XRPD analysis is illustrated in Table 6.

3-[5-(2-fluorophenyl)-[1,2,4]oxadiazol-3-yl]-benzoic acid (UNMEASURED QUANTITY; FORM B) was stressed in 75% relative humidity at 40° C. for six days. The solids that formed were isolated and characterized by XRPD as Form B. XRPD analysis is illustrated in Table 7.

5.2 Analytical Procedures

The following methods of solid-state analysis provide examples of how the solid forms of 3-[5-(2-fluorophenyl)-[1,2,4]oxadiazol-3-yl]-benzoic acid of the present invention may be characterized. The specific methods described below were employed to obtain the solid-state characterization data described herein.

5.2.1 X-Ray Powder Diffraction (XRPD)

Certain XRPD analyses were performed using a Shimadzu XRD-6000 X-ray powder diffractometer using Cu Kα radiation. The instrument is equipped with a long fine focus X-ray tube. The tube voltage and amperage were set to 40 kV and 40 mA, respectively. The divergence and scattering slits were set at 1° and the receiving slit was set at 0.15 mm. Diffracted radiation was detected by a NaI scintillation detector. A θ-2θ continuous scan at 3°/min (0.4 sec/0.02° step) from 2.5 to 40° 2θ was used. A silicon standard was analyzed to check the instrument alignment. Data were collected and analyzed using XRD-6100/7000 v. 5.0. Samples were prepared for analysis by placing them in a sample holder.

Certain XRPD analyses were performed using an Inel XRG-3000 diffractometer equipped with a CPS (Curved Position Sensitive) detector with a 2θ range of 120°. Real time data were collected using Cu—Kα radiation at a resolution of 0.03° 2θ. The tube voltage and amperage were set to 40 kV and 30 mA, respectively. The monochromator slit was set at 5 mm by 160 µm. The pattern is displayed from 2.5-40° 2θ. An aluminum sample holder with silicon insert was used/or/Samples were prepared for analysis by packing them into thin-walled glass capillaries. Each capillary was mounted onto a goniometer head that is motorized to permit spinning of the capillary during data acquisition. The samples were analyzed for 300 sec. Instrument calibration was performed using a silicon reference standard.

Certain XRPD patterns were collected with a Bruker D-8 Discover diffractometer and Bruker's General Area Diffraction Detection System (GADDS, v. 4.1.20). An incident beam of Cu Kα radiation was produced using a fine-focus tube (40 kV, 40 mA), a Gael mirror, and a 0.5 mm double-pinhole collimator. A specimen of the sample was packed in a capillary and secured to a translation stage. A video camera and laser were used to position the area of interest to intersect the incident beam in transmission geometry. The incident beam was scanned to optimize orientation statistics. A beam-stop was used to minimize air scatter from the incident beam at low angles. Diffraction patterns were collected using a Hi-Star area detector located 15 cm from the sample and processed using GADDS. The intensity in the GADDS image of the diffraction pattern was integrated using a step size of 0.04° 2θ. The integrated patterns display diffraction intensity as a function of 2θ. Prior to the analysis a silicon standard was analyzed to verify the Si 111 peak position.

Certain XRPD files generated from Inel XRPD instruments were converted to Shimadzu .raw file using File Monkey version 3.0.4. The Shimadzu .raw file was processed by the Shimadzu XRD-6000 version 2.6 software to automatically find peak positions. The "peak position" means the maximum intensity of a peaked intensity profile. Parameters used in peak selection are shown in the lower half of each parameter set of the data. The following processes were used with the Shimadzu XRD-6000 "Basic Process" version 2.6 algorithm:

Smoothing was done on all patterns.
The background was subtracted to find the net, relative intensity of the peaks.
A peak from Cu K alpha2 (1.5444 Å) wavelength was subtracted from the peak generated by Cu K alpha1 (1.5406 Å) peak at 50% intensity for all patterns.

5.2.2 Differential Scanning Calorimetry (DSC)

Differential scanning calorimetry (DSC) was performed using a TA Instruments differential scanning calorimeter 2920. The sample was placed into an aluminum DSC pan, and the weight accurately recorded. The pan was covered with a lid and then crimped. The sample cell was equilibrated at 25° C. and heated under a nitrogen purge at a rate of 10° C./min, up to a final temperature of 350° C. Indium metal was used as the calibration standard. Reported temperatures are at the transition maxima.

5.2.3 Thermogravimetric Analysis (TGA)

Thermogravimetric (TG) analyses were performed using a TA Instruments 2950 thermogravimetric analyzer. Each sample was placed in an aluminum sample pan and inserted into the TG furnace. The furnace was (first equilibrated at 35° C., then) heated under nitrogen at a rate of 10° C./min, up to a final temperature of 350° C. Nickel and Alumel™ were used as the calibration standards.

5.2.4 Dynamic Vapor Sorption/Desorption (DVS)

Moisture sorption/desorption data were collected on a VTI SGA-100 Vapor Sorption Analyzer. Sorption and desorption data were collected over a range of 5% to 95% relative humidity (RH) at 10% RH intervals under a nitrogen purge. Samples were not dried prior to analysis. Equilibrium criteria used for analysis were less than 0.0100% weight change in 5 minutes, with a maximum equilibration time of 3 hours if the weight criterion was not met. Data were not corrected for the initial moisture content of the samples. NaCl and PVP were used as calibration standards.

5.2.5 Karl Fischer (KF)

Coulometric Karl Fischer (KF) analysis for water determination was performed using a Mettler Toledo DL39 Karl Fischer titrator. Approximately 21 mg of sample was placed in the KF titration vessel containing Hydranal-Coulomat AD and mixed for 42-50 seconds to ensure dissolution. The sample was then titrated by means of a generator electrode which produces iodine by electrochemical oxidation: 2 I-=>$I_2$+2e. Three replicates were obtained to ensure reproducibility.

5.2.6 Hotstae Microscopy

Hotstage microscopy was performed using a Linkam FTIR 600 hotstage with a TMS93 controller mounted on a Leica DM LP microscope equipped with a Spot Insight color camera for acquiring images. Images are acquired using Spot Advanced software version 4.5.9 build date Jun. 9, 2005, unless noted. The camera was white balanced prior to use. Samples were observed and acquired using a 20×0.40 N.A. long working distance objective with crossed polars and first order red compensator. Samples were placed on a coverslip. Another coverslip was then placed over the sample. Each sample was visually observed as the stage was heated. The hotstage was calibrated using USP melting point standards.

5.2.7 Solid State Cross-Polarized Magic Angle Spinning $^{13}$C Nuclear Magnetic Resonance Spectroscopy ($^{13}$C CP/MAS ssNMR)

Samples were prepared for solid-state NMR spectroscopy by packing them into 4 mm PENCIL type zirconia rotors. Scans were collected at ambient temperature with a relaxation delay of 120.000 s, a pulse width of 2.2 µs (90.0 deg), an acquisition time of 0.030 s, and a spectral width of 44994.4 Hz (447.520 ppm). A total of 100 scans were collected. Cross polarization was achieved with using $^{13}$C as the observed nucleus and $^{1}$H as the decoupled nucleus with a contact time of 10.0 ms. A magic angle spinning rate of 12000 Hz was used. Spectra are externally referenced to glycine at 176.5 ppm.

Those skilled in the art will recognize, or be able to ascertain using no more than routine experimentation, many equivalents to the specific embodiments of the invention described herein. Such equivalents are intended to be encompassed by the following claims. All publications, patents and patent applications mentioned in this specification are herein incorporated by reference into the specification to the same extent as if each individual publication, patent or patent application was specifically and individually indicated to be incorporated herein by reference.

5.2.8 Single-Crystal X-Ray Diffraction

Sample Preparation

The crystals utilized for Form A structure determination were prepared by sublimation of the Form A. The crystals were removed from the cold finger after the sample was heated between 155-206° C. for approximately 90 minutes. (Table 3 Experimental)

Data Collection

A colorless needle of $C_{15}H_9FN_2O_3$ having approximate dimensions of 0.44×0.13×0.03 mm, was mounted on a glass fiber in random orientation. Preliminary examination and data collection were performed with Mo $K_\alpha$ radiation ($\lambda$=0.71073 Å) on a Nonius KappaCCD diffractometer. Refinements were performed on an LINUX PC using SHELX97 (Sheldrick, G. M. SHELX97, *A Program for Crystal Structure Refinement*, University of Gottingen, Germany, 1997).

Cell constants and an orientation matrix for data collection were obtained from least-squares refinement using the setting angles of 13862 reflections in the range 2°<θ<24°. The refined mosaicity from DENZO/SCALEPACK (Otwinowski, Z.; Minor, W. *Methods Enzymol*. 1997, 276, 307) was 0.33° indicating good crystal quality. The space group was determined by the program XPREP (Bruker, XPREP in SHELXTL v. 6.12., Bruker AXS Inc., Madison, Wis., USE, 2002). From the systematic presence of the following conditions: h0l h+l=2n; 0k0 k=2n, and from subsequent least-squares refinement, the space group was determined to be P2$_1$/n (no. 14).

The data were collected to a maximum 2θ value of 2469°, at a temperature of 150±1 K.

Data Reduction

Frames were integrated with DENZO-SMN (Otwinowski, Z.; Minor, W. *Methods Enzymol*. 1997, 276, 307). A total of 13862 reflections were collected, of which 3201 were unique.

Lorentz and polarization corrections were applied to the data. The linear absorption coefficient is 0.110 mm$^{-1}$ for Mo $K_\alpha$ radiation. An empirical absorption correction using SCALEPACK (Otwinowski, Z.; Minor, W. *Methods Enzymol*. 1997, 276, 307) was applied. Transmission coefficients ranged from 0.951 to 0.997. A secondary extinction correction was applied (Sheldrick, G. M. SHELX97, *A Program for Crystal Structure Refinement*, University of Gottingen, Germany, 1997). The final coefficient, refined in least-squares, was 0.0046 (in absolute units). Intensities of equivalent reflections were averaged. The agreement factor for the averaging was 10.1% based on intensity.

Structure Solution and Refinement

The structure was solved by direct methods using SIR2004 (Burla, M. C., et al., *J. Appl. Cryst.* 2005, 38, 381). The remaining atoms were located in succeeding difference Fourier syntheses. Hydrogen atoms were included in the refinement but restrained to ride on the atom to which they are bonded. The structure was refined in full-matrix least-squares by minimizing the function:

$$\Sigma w(|F_o|^2-|F_c|^2)^2$$

The weight w is defined as $1/[\sigma^2(F_o^2)+(0.0975P)^2+(0.0000P)]$, where $P=(F_o^2+2F_c^2)/3$.

Scattering factors were taken from the "International Tables for Crystallography" (International Tables for Crystallography, Vol. C, Kluwer Academic Publishers: Dordrecht, The Netherlands, 1992, Tables 4.2.6.8 and 6.1.1.4). Of the 3201 reflections used in the refinements, only the reflections with $F_o^2>2\sigma(F_o^2)$ were used in calculating R. A total of 2010 reflections were used in the calculation. The final cycle of refinement included 382 variable parameters and converged (largest parameter shift was <0.01 times its estimated standard deviation) with unweighted and weighted agreement factors of:

$$R=\Sigma|F_o-F_c|/\Sigma F_o=0.062$$

$$R_w = \sqrt{(\Sigma w(F_o^2-F_c^2)^2/\Sigma w(F_o^2)^2)} = 0.152$$

The standard deviation of an observation of unit weight was 1.01. The highest peak in the final difference Fourier had a height of 0.64 e/Å$^3$. The minimum negative peak had a height of −0.33 e/Å$^3$.

Calculated X-Ray Powder Diffraction (XRPD) Pattern

A calculated XRPD pattern was generated for Cu radiation using PowderCell 2.3 (PowderCell for Windows Version 2.3 Kraus, W.; Nolze, G. Federal Institute for Materials Research and Testing, Berlin Germany, EU, 1999) and the atomic coordinates, space group, and unit cell parameters from the single crystal data.

ORTEP and Packing Diagrams

The ORTEP diagram was prepared using ORTEP III (Johnson, C. K. ORTEPIII, Report ORNL-6895, Oak Ridge National Laboratory, TN, U.S.A. 1996, and OPTEP-3 for Windows V1.05, Farrugia, L. J., *J. Appl. Cryst.* 1997, 30, 565). Atoms are represented by 50% probability anisotropic thermal ellipsoids. Packing diagrams were prepared using CAMERON (Watkin, D. J. et al., CAMERON, Chemical Crystallography Laboratory, University of Oxford, Oxford, 1996) modeling.

Results and Discussion

The monoclinic cell parameters and calculated volume of Form A are: a=24.2240(10) Å, b=3.74640(10) Å, c=27.4678 (13) Å, α=90.00°, β=92.9938(15)°, γ=90.00°, V=2489.38

(17) Å$^3$. The molecular weight is 284.25 g/mol$^{-1}$ and Z=8 (where Z is the number of drug molecules per asymmetric unit) resulting in a calculated density (d$_{calc}$, g cm$^{-3}$) of 1.517 g cm$^{-3}$ for this crystal structure. The space group was determined to be P2$_1$/n (no. 14), which is an achiral space group. A summary of the crystal data and crystallographic data collection parameters are provided as follows:

| | |
|---|---|
| formula | C$_{15}$H$_9$FN$_2$O$_3$ |
| formula weight | 284.25 |
| space group | P 1 21/n 1 (No. 14) |
| a, Å | 24.2240(10) |
| b, Å | 3.74640(10) |
| c, Å | 27.4678(13) |
| b, deg | 92.9938(15) |
| V, Å$^3$ | 2489.38(17) |
| Z | 8 |
| d$_{calc}$, g cm$^{-3}$ | 1.517 |
| crystal dimensions, mm | 0.44 × 0.13 × 0.03 |
| temperature, K | 150. |
| radiation (wavelength, Å) | Mo K$_\alpha$ (0.71073) |
| monochromator | graphite |
| linear abs coef, mm$^{-1}$ | 0.110 |
| absorption correction applied | empirical |
| transmission factors: min, max | 0.951 to 0.997 |
| diffractometer | Nonius KappaCCD |
| h, k, l range | 0 to 28 0 to 4 −32 to 32 |
| 2q range, deg | 4.45-49.38 |
| mosaicity, deg | 0.33 |
| programs used | SHELXTL |
| F$_{000}$ | 1168.0 |
| weighting | 1/[s$^2$(F$_o^2$) + (0.0975P)$^2$ + 0.0000P] where P = (F$_o^2$ + 2F$_c^2$)/3 |
| data collected | 13862 |
| unique data | 3201 |
| R$_{int}$ | 0.101 |
| data used in refinement | 3201 |
| cutoff used in R-factor calculations | F$_o^2$ > 2.0s(F$_o^2$) |
| data with I > 2.0s(I) | 2010 |
| refined extinction coef | 0.0046 |
| number of variables | 382 |
| largest shift/esd in final cycle | 0.00 |
| R(F$_o$) | 0.062 |
| R$_w$(F$_o^2$) | 0.152 |
| goodness of fit | 1.006 |

The quality of the structure obtained is high to moderate, as indicated by the R-value of 0.062 (6.2%). Usually R-values in the range of 0.02 to 0.06 are quoted for the most reliably determined structures. While the quality of the crystal structure is slightly outside the accepted range for most reliably determined structures, the data is of sufficient quality to ensure to location of the atomic positions in the molecular structure is correct.

An ORTEP drawing of Form A is shown in FIG. 11. The asymmetric unit shown in contains a dimer of two molecules arranged to form a possible hydrogen bond through the adjacent carboxylic acid groups. Since the acid protons were not located from the Fourier map it is assumed the molecules are neutral. A packing diagram of Form A, viewed down the crystallographic b axis, is shown in FIG. 9.

The simulated XRPD pattern of Form A, shown in FIG. 10, was generated from the single crystal data, and is in good agreement with the experimental XRPD pattern of Form A (see, e.g., FIG. 1). Differences in intensities can arise from preferred orientation. Preferred orientation is the tendency for crystals, usually plates or needles, to align themselves with some degree of order. Preferred orientation can affect peak intensities, but not peak positions, in XRPD patterns. Slight shifts in peak location can arise from the fact that the experimental powder pattern was collected at ambient temperature, and the single crystal data was collected at 150 K. Low temperatures are used in single crystal analysis to improve the quality of the structure.

Table 1 shows the fractional atomic coordinates for the asymmetric unit of Form A.

TABLE 1

Positional Parameters and Their Estimated Standard Deviations for Form A

| Atom | x | y | z | U(Å$^2$) |
|---|---|---|---|---|
| F(122) | 0.43198(12) | 0.7655(8) | −0.17546(10) | 0.0487(10) |
| F(222) | −0.20343(15) | 0.7129(10) | 0.06378(14) | 0.0781(14) |
| O(13) | 0.42977(13) | 0.4875(8) | −0.08927(11) | 0.0324(10) |
| O(23) | −0.12941(13) | 0.4507(9) | 0.12653(12) | 0.0402(10) |
| O(151) | 0.25519(13) | 0.4795(9) | 0.10765(12) | 0.0382(10) |
| O(152) | 0.29215(13) | 0.2155(9) | 0.17515(12) | 0.0403(10) |
| O(251) | 0.16226(13) | 0.4813(9) | 0.15012(12) | 0.0385(10) |
| O(252) | 0.19645(13) | 0.1939(9) | 0.21659(12) | 0.0393(10) |
| N(11) | 0.35817(15) | 0.5856(9) | −0.04386(14) | 0.0279(10) |
| N(14) | 0.44373(16) | 0.3409(10) | −0.04263(14) | 0.0327(12) |
| N(21) | −0.04134(16) | 0.5165(9) | 0.11065(14) | 0.0305(12) |
| N(24) | −0.09772(17) | 0.3201(11) | 0.16787(15) | 0.0388(14) |
| C(12) | 0.37827(18) | 0.6256(11) | −0.08637(17) | 0.0266(14) |
| C(15) | 0.40019(19) | 0.4091(11) | −0.01823(17) | 0.0261(14) |
| C(22) | −0.0926(2) | 0.5601(12) | 0.09502(18) | 0.0319(15) |
| C(25) | −0.0471(2) | 0.3690(11) | 0.15580(17) | 0.0302(15) |
| C(121) | 0.35225(19) | 0.7961(11) | −0.12930(17) | 0.0291(14) |
| C(122) | 0.3784(2) | 0.8567(12) | −0.17244(18) | 0.0345(15) |
| C(123) | 0.3519(2) | 1.0117(12) | −0.21257(19) | 0.0407(17) |
| C(124) | 0.2973(2) | 1.1101(13) | −0.21014(19) | 0.0416(17) |
| C(125) | 0.2694(2) | 1.0543(12) | −0.1677(2) | 0.0409(17) |
| C(126) | 0.2966(2) | 0.8996(12) | −0.12784(18) | 0.0349(15) |
| C(151) | 0.39702(19) | 0.3013(11) | 0.03319(16) | 0.0260(14) |
| C(152) | 0.34897(19) | 0.3623(11) | 0.05704(16) | 0.0261(15) |
| C(153) | 0.34631(18) | 0.2594(11) | 0.10554(16) | 0.0253(14) |
| C(154) | 0.39150(19) | 0.0970(11) | 0.13029(17) | 0.0279(14) |
| C(155) | 0.43977(19) | 0.0412(11) | 0.10614(17) | 0.0291(15) |
| C(156) | 0.44250(19) | 0.1421(11) | 0.05765(17) | 0.0292(15) |
| C(157) | 0.2955(2) | 0.3188(12) | 0.13209(18) | 0.0312(15) |
| C(221) | −0.1109(2) | 0.7083(12) | 0.04727(19) | 0.0388(17) |
| C(222) | −0.1643(3) | 0.7823(15) | 0.0331(2) | 0.053(2) |
| C(223) | −0.1825(3) | 0.9272(15) | −0.0122(3) | 0.064(2) |
| C(224) | −0.1415(4) | 0.9930(16) | −0.0433(3) | 0.068(3) |
| C(225) | −0.0870(3) | 0.9202(15) | −0.0316(2) | 0.066(2) |
| C(226) | −0.0678(3) | 0.7766(12) | 0.01365(17) | 0.0543(19) |
| C(251) | 0.00110(19) | 0.2695(12) | 0.18877(17) | 0.0300(15) |
| C(252) | 0.05426(19) | 0.3352(11) | 0.17481(17) | 0.0289(15) |
| C(253) | 0.09949(19) | 0.2449(11) | 0.20524(17) | 0.0277(15) |
| C(254) | 0.0919(2) | 0.0940(11) | 0.25087(17) | 0.0296(15) |
| C(255) | 0.0389(2) | 0.0335(11) | 0.26491(17) | 0.0300(15) |
| C(256) | −0.0064(2) | 0.1185(12) | 0.23430(17) | 0.0322(15) |
| C(257) | 0.1559(2) | 0.3165(12) | 0.18902(17) | 0.0305(15) |
| H(123) | 0.371 | 1.050 | −0.241 | 0.048 |
| H(124) | 0.278 | 1.217 | −0.238 | 0.050 |
| H(125) | 0.232 | 1.123 | −0.166 | 0.049 |
| H(126) | 0.278 | 0.862 | −0.099 | 0.042 |
| H(151) | 0.227 | 0.491 | 0.125 | 0.057 |
| H(152) | 0.318 | 0.473 | 0.041 | 0.031 |
| H(154) | 0.389 | 0.025 | 0.163 | 0.033 |
| H(155) | 0.471 | −0.066 | 0.123 | 0.035 |
| H(156) | 0.475 | 0.103 | 0.041 | 0.035 |
| H(223) | −0.220 | 0.975 | −0.020 | 0.077 |
| H(224) | −0.151 | 1.094 | −0.074 | 0.082 |
| H(225) | −0.061 | 0.969 | −0.055 | 0.080 |
| H(226) | −0.030 | 0.729 | 0.021 | 0.065 |
| H(252) | 0.226 | 0.213 | 0.202 | 0.059 |
| H(254) | 0.123 | 0.034 | 0.272 | 0.035 |
| H(255) | 0.033 | −0.068 | 0.296 | 0.036 |
| H(256) | −0.043 | 0.074 | 0.244 | 0.039 |
| H(25A) | 0.060 | 0.443 | 0.144 | 0.035 |

U$_{eq}$ = (1/3)Σ$_i$Σ$_j$ U$_{ij}$a*$_i$a*$_j$a$_i$·a$_j$
Hydrogen atoms are included in calculation of structure factors but not refined

TABLE 2

Peak Positions of Form A from Calculated XRPD Pattern Generated from Single Crystal Data

| Position (°2θ)[a] | d-spacing | I/Io[c] |
|---|---|---|
| 4.74 | 18.63 | 3.24 |
| 4.99 | 17.69 | 20.99 |
| 6.44 | 13.72 | 4.46 |
| 7.30 | 12.10 | 6.46 |
| 10.15 | 8.70 | 32.47 |
| 10.51 | 8.41 | 1.90 |
| 11.27 | 7.85 | 6.14 |
| 11.59 | 7.63 | 13.97 |
| 12.90 | 6.86 | 15.05 |
| 14.25 | 6.21 | 100.00 |
| 14.50 | 6.10 | 8.25 |
| 14.64 | 6.05 | 75.70 |
| 15.17 | 5.84 | 65.12 |
| 15.69 | 5.64 | 47.56 |
| 16.31 | 5.43 | 8.61 |
| 16.37 | 5.41 | 8.11 |
| 16.74 | 5.29 | 14.82 |
| 18.44 | 4.81 | 2.04 |
| 18.78 | 4.72 | 3.13 |
| 19.04 | 4.66 | 4.05 |
| 19.07 | 4.65 | 3.81 |
| 19.40 | 4.57 | 2.85 |
| 20.03 | 4.43 | 11.28 |
| 20.06 | 4.42 | 5.41 |
| 20.30 | 4.37 | 1.92 |
| 20.39 | 4.35 | 10.87 |
| 21.11 | 4.20 | 21.30 |
| 21.20 | 4.19 | 7.07 |
| 22.03 | 4.03 | 4.07 |
| 22.64 | 3.92 | 4.72 |
| 23.16 | 3.84 | 4.71 |
| 23.86 | 3.73 | 2.64 |
| 23.95 | 3.71 | 9.76 |
| 24.21 | 3.67 | 12.14 |
| 24.27 | 3.67 | 32.98 |
| 24.61 | 3.61 | 61.89 |
| 24.84 | 3.58 | 3.05 |
| 24.86 | 3.58 | 8.00 |
| 24.94 | 3.57 | 7.15 |
| 25.00 | 3.56 | 2.17 |
| 25.02 | 3.56 | 2.09 |
| 25.13 | 3.54 | 10.36 |
| 25.61 | 3.48 | 1.67 |
| 25.79 | 3.45 | 3.04 |
| 25.87 | 3.44 | 25.14 |
| 26.02 | 3.42 | 15.19 |
| 26.20 | 3.40 | 3.41 |
| 26.48 | 3.36 | 10.64 |
| 26.87 | 3.31 | 3.11 |
| 26.87 | 3.32 | 5.65 |
| 27.08 | 3.29 | 5.60 |
| 27.10 | 3.29 | 33.71 |
| 27.16 | 3.28 | 93.68 |
| 27.26 | 3.27 | 82.52 |
| 27.45 | 3.25 | 4.42 |
| 27.92 | 3.19 | 5.61 |
| 28.05 | 3.18 | 3.96 |
| 28.20 | 3.16 | 59.41 |
| 28.28 | 3.15 | 3.04 |
| 28.53 | 3.13 | 6.29 |
| 28.83 | 3.09 | 13.36 |
| 28.93 | 3.08 | 15.74 |
| 28.96 | 3.08 | 6.42 |
| 29.05 | 3.07 | 3.93 |
| 29.18 | 3.06 | 2.42 |
| 29.24 | 3.05 | 2.10 |
| 29.42 | 3.03 | 2.64 |
| 29.52 | 3.02 | 2.19 |
| 29.57 | 3.02 | 15.65 |
| 29.94 | 2.98 | 2.66 |
| 30.00 | 2.98 | 4.98 |
| 30.43 | 2.94 | 1.68 |
| 30.58 | 2.92 | 1.21 |
| 30.79 | 2.90 | 1.79 |
| 30.93 | 2.89 | 1.07 |
| 31.07 | 2.88 | 3.23 |
| 31.18 | 2.87 | 7.65 |
| 31.42 | 2.84 | 2.68 |
| 31.97 | 2.80 | 2.16 |
| 32.46 | 2.76 | 1.99 |
| 32.65 | 2.74 | 1.23 |
| 32.88 | 2.72 | 1.02 |
| 33.13 | 2.70 | 2.89 |
| 33.17 | 2.70 | 4.30 |
| 33.40 | 2.68 | 2.97 |
| 33.64 | 2.66 | 2.39 |
| 33.90 | 2.64 | 1.46 |
| 34.25 | 2.62 | 2.54 |
| 34.74 | 2.58 | 1.40 |
| 35.18 | 2.55 | 1.60 |
| 35.59 | 2.52 | 1.21 |
| 35.96 | 2.50 | 1.50 |
| 36.64 | 2.45 | 7.44 |

[a] I/Io = relative intensity
b. Peaks having I/Io = relative intensity less than 1 and peak positions greater than 36.6 °2θ are not displayed

TABLE 3

Peak Positions of Form A Experimental XRPD Pattern

| Position (°2θ)[a] | d-spacing | I | I/Io[c] |
|---|---|---|---|
| 4.96 | 17.79 | 59 | 4 |
| 6.39 | 13.83 | 52 | 4 |
| 10.10 | 8.75 | 417 | 31 |
| 11.54 | 7.66 | 144 | 11 |
| 12.62 | 7.01 | 101 | 7 |
| 12.81 | 6.91 | 341 | 25 |
| 13.92 | 6.36 | 197 | 14 |
| 14.16 | 6.25 | 737 | 54 |
| 14.55 | 6.08 | 621 | 46 |
| 14.88 | 5.95 | 379 | 28 |
| 15.07 | 5.87 | 1364 | 100 |
| 15.58 | 5.68 | 223 | 16 |
| 16.27 | 5.44 | 288 | 21 |
| 16.61 | 5.33 | 405 | 30 |
| 18.74 | 4.73 | 52 | 4 |
| 18.94 | 4.68 | 84 | 6 |
| 19.28 | 4.60 | 115 | 8 |
| 19.94 | 4.45 | 248 | 18 |
| 20.27 | 4.38 | 240 | 18 |
| 20.74 | 4.28 | 131 | 10 |
| 20.97 | 4.23 | 602 | 44 |
| 21.22 | 4.18 | 126 | 9 |
| 21.93 | 4.05 | 44 | 3 |
| 22.58 | 3.93 | 60 | 4 |
| 22.80 | 3.90 | 88 | 6 |
| 23.00 | 3.86 | 146 | 11 |
| 23.79 | 3.74 | 173 | 13 |
| 24.14 | 3.68 | 161 | 12 |
| 24.46 | 3.64 | 61 | 4 |
| 25.44 | 3.50 | 104 | 8 |
| 25.64 | 3.47 | 87 | 6 |
| 26.07 | 3.42 | 111 | 8 |
| 26.34 | 3.38 | 100 | 7 |
| 26.74 | 3.33 | 559 | 41 |
| 27.06 | 3.29 | 55 | 4 |
| 27.79 | 3.21 | 173 | 13 |
| 28.42 | 3.14 | 154 | 11 |
| 29.09 | 3.07 | 63 | 5 |
| 30.48 | 2.93 | 55 | 4 |

[a] I/Io = relative intensity
b. Bold denotes characteristic peak set (no peaks within 0.2 °2θ relative to PTC124 Form B files 169490, 172972, 172173, 170901, 169284, and 168717.

TABLE 4

Peak Positions of Form B XRPD Pattern (file 169490)

| Position (°2θ)[a] | d-spacing | I | I/Io[c] |
|---|---|---|---|
| 6.14 | 14.38 | 73 | 7 |
| 6.39 | 13.82 | 386 | 35 |
| 6.96 | 12.70 | 57 | 5 |
| 7.92 | 11.16 | 171 | 15 |
| 10.78 | 8.20 | 163 | 15 |
| 12.44 | 7.11 | 66 | 6 |
| 12.61 | 7.01 | 163 | 15 |
| 12.88 | 6.87 | 41 | 4 |
| 13.52 | 6.54 | 261 | 23 |
| 13.78 | 6.42 | 351 | 31 |
| 13.97 | 6.33 | 1115 | 100 |
| 14.30 | 6.19 | 35 | 3 |
| 15.46 | 5.73 | 46 | 4 |
| 15.68 | 5.65 | 227 | 20 |
| 15.89 | 5.57 | 754 | 68 |
| 16.33 | 5.42 | 204 | 18 |
| 16.76 | 5.29 | 105 | 9 |
| 17.03 | 5.20 | 485 | 43 |
| 20.10 | 4.41 | 603 | 54 |
| 21.03 | 4.22 | 110 | 10 |
| 23.34 | 3.81 | 42 | 4 |
| 23.86 | 3.73 | 199 | 18 |
| 24.18 | 3.68 | 294 | 26 |
| 24.42 | 3.64 | 120 | 11 |
| 24.64 | 3.61 | 49 | 4 |
| 26.62 | 3.35 | 121 | 11 |
| 26.96 | 3.30 | 134 | 12 |
| 27.29 | 3.27 | 949 | 85 |
| 27.64 | 3.22 | 155 | 14 |
| 27.96 | 3.19 | 93 | 8 |
| 28.81 | 3.10 | 101 | 9 |
| 31.05 | 2.88 | 55 | 5 |
| 32.38 | 2.76 | 43 | 4 |
| 32.58 | 2.75 | 39 | 3 |
| 36.23 | 2.48 | 89 | 8 |
| 37.81 | 2.38 | 38 | 3 |
| 38.28 | 2.35 | 53 | 5 |
| 38.44 | 2.34 | 83 | 7 |
| 39.16 | 2.30 | 45 | 4 |

[a] I/Io = relative intensity.
b. Bold denotes characteristic peak set compared to Form A.

TABLE 5

Peak Positions of Form B (shifted 1) XRPD Pattern (file 168717)

| Position (°2θ)[a] | d-spacing | I | I/Io[c] |
|---|---|---|---|
| 6.42 | 13.75 | 214 | 34 |
| 7.00 | 12.63 | 23 | 4 |
| 7.89 | 11.20 | 98 | 15 |
| 10.85 | 8.15 | 97 | 15 |
| 12.61 | 7.01 | 117 | 18 |
| 12.92 | 6.85 | 29 | 5 |
| 13.47 | 6.57 | 208 | 33 |
| 13.97 | 6.33 | 558 | 88 |
| 15.81 | 5.60 | 635 | 100 |
| 16.45 | 5.38 | 143 | 23 |
| 17.12 | 5.18 | 320 | 50 |
| 20.05 | 4.42 | 544 | 86 |
| 21.05 | 4.22 | 66 | 10 |
| 23.92 | 3.72 | 110 | 17 |
| 24.28 | 3.66 | 21 | 3 |
| 27.00 | 3.30 | 48 | 8 |
| 27.39 | 3.25 | 126 | 20 |
| 27.84 | 3.20 | 32 | 5 |
| 28.04 | 3.18 | 68 | 11 |
| 28.94 | 3.08 | 90 | 14 |
| 31.10 | 2.87 | 35 | 6 |
| 32.58 | 2.75 | 42 | 7 |
| 36.11 | 2.49 | 89 | 14 |
| 37.71 | 2.38 | 19 | 3 |
| 38.15 | 2.36 | 20 | 3 |
| 38.61 | 2.33 | 52 | 8 |

[a] I/Io = relative intensity
b. Bold denotes characteristic peak set compared to Form A.

TABLE 6

Peak Positions of Form B (shifted 2) XRPD Pattern (file 172972)

| Position (°2θ)[a] | d-spacing | I | I/Io[c] |
|---|---|---|---|
| 6.10 | 14.48 | 155 | 3 |
| 6.38 | 13.84 | 1068 | 23 |
| 6.54 | 13.50 | 1371 | 29 |
| 7.10 | 12.44 | 270 | 6 |
| 8.02 | 11.02 | 653 | 14 |
| 10.91 | 8.11 | 376 | 8 |
| 12.71 | 6.96 | 195 | 4 |
| 13.50 | 6.55 | 601 | 13 |
| 13.62 | 6.50 | 404 | 9 |
| 13.86 | 6.38 | 702 | 15 |
| 14.10 | 6.27 | 4633 | 99 |
| 15.56 | 5.69 | 158 | 3 |
| 15.70 | 5.64 | 402 | 9 |
| 15.91 | 5.57 | 3422 | 73 |
| 16.55 | 5.35 | 673 | 14 |
| 16.96 | 5.22 | 283 | 6 |
| 17.22 | 5.15 | 1639 | 35 |
| 17.50 | 5.06 | 150 | 3 |
| 19.82 | 4.48 | 242 | 5 |
| 20.08 | 4.42 | 1950 | 42 |
| 20.34 | 4.36 | 209 | 4 |
| 21.15 | 4.20 | 718 | 15 |
| 23.78 | 3.74 | 208 | 4 |
| 23.93 | 3.72 | 508 | 11 |
| 24.38 | 3.65 | 412 | 9 |
| 24.56 | 3.62 | 184 | 4 |
| 26.88 | 3.31 | 198 | 4 |
| 27.16 | 3.28 | 219 | 5 |
| 27.48 | 3.24 | 4657 | 100 |
| 27.88 | 3.20 | 231 | 5 |
| 28.04 | 3.18 | 183 | 4 |
| 28.78 | 3.10 | 353 | 8 |
| 29.02 | 3.07 | 948 | 20 |
| 32.71 | 2.74 | 233 | 5 |
| 36.01 | 2.49 | 639 | 14 |
| 38.10 | 2.36 | 253 | 5 |
| 38.56 | 2.33 | 216 | 5 |
| 39.38 | 2.29 | 179 | 4 |

[a] I/Io = relative intensity
b. Bold denotes characteristic peak set compared to Form A.

TABLE 7

Peak Positions of Form B (shifted 3) XRPD Pattern (file 172173)

| Position (°2θ)[a] | d-spacing | I | I/Io[c] |
|---|---|---|---|
| 1.79 | 49.38 | 398 | 3 |
| 2.30 | 38.42 | 1002 | 9 |
| 2.57 | 34.38 | 1008 | 9 |
| 2.78 | 31.78 | 974 | 8 |
| 3.29 | 26.85 | 786 | 7 |
| 3.59 | 24.61 | 739 | 6 |
| 3.89 | 22.71 | 634 | 5 |
| 4.07 | 21.71 | 617 | 5 |
| 4.34 | 20.35 | 553 | 5 |
| 4.49 | 19.67 | 476 | 4 |
| 4.76 | 18.56 | 415 | 4 |
| 5.06 | 17.46 | 347 | 3 |
| 6.47 | 13.66 | 9496 | 82 |

TABLE 7-continued

Peak Positions of Form B (shifted 3) XRPD Pattern (file 172173)

| Position (°2θ)[a] | d-spacing | I | I/Io[c] |
|---|---|---|---|
| 6.91 | 12.79 | 1606 | 14 |
| 7.96 | 11.09 | 2771 | 24 |
| 10.89 | 8.12 | 3389 | 29 |
| 12.87 | 6.87 | 2022 | 18 |
| 13.58 | 6.52 | 381 | 3 |
| 13.99 | 6.32 | 4752 | 41 |
| 15.97 | 5.55 | 1724 | 15 |
| 16.48 | 5.38 | 752 | 7 |
| 17.10 | 5.18 | 1790 | 16 |
| 20.00 | 4.44 | 505 | 4 |
| 20.36 | 4.36 | 1069 | 9 |
| 21.04 | 4.22 | 501 | 4 |
| 23.40 | 3.80 | 906 | 8 |
| 24.29 | 3.66 | 6591 | 57 |
| 24.89 | 3.57 | 522 | 5 |
| 26.87 | 3.32 | 1823 | 16 |
| 27.49 | 3.24 | 11543 | 100 |
| 27.80 | 3.21 | 1924 | 17 |
| 28.07 | 3.18 | 353 | 3 |
| 29.08 | 3.07 | 434 | 4 |
| 38.61 | 2.33 | 376 | 3 |

[a] I/Io = relative intensity.
b. Bold denotes characteristic peak set compared to Form A.

TABLE 8

Peak Positions of Form B (PO) XRPD Pattern (file 170901)

| Position (°2θ)[a] | d-spacing | I | I/Io[c] |
|---|---|---|---|
| 6.22 | 14.20 | 356 | 8 |
| 6.51 | 13.57 | 1332 | 30 |
| 7.13 | 12.39 | 171 | 4 |
| 8.17 | 10.81 | 727 | 17 |
| 10.91 | 8.11 | 484 | 11 |
| 12.87 | 6.87 | 355 | 8 |
| 13.80 | 6.41 | 930 | 21 |
| 14.12 | 6.27 | 4251 | 97 |
| 14.28 | 6.20 | 2569 | 59 |
| 15.78 | 5.61 | 172 | 4 |
| 16.23 | 5.46 | 4368 | 100 |
| 16.54 | 5.36 | 684 | 16 |
| 17.15 | 5.17 | 1377 | 32 |
| 20.33 | 4.36 | 1057 | 24 |
| 21.22 | 4.18 | 475 | 11 |
| 21.36 | 4.16 | 290 | 7 |
| 23.94 | 3.71 | 578 | 13 |
| 24.30 | 3.66 | 201 | 5 |
| 27.30 | 3.26 | 217 | 5 |
| 27.58 | 3.23 | 303 | 7 |
| 28.00 | 3.18 | 262 | 6 |
| 28.74 | 3.10 | 239 | 5 |
| 28.96 | 3.08 | 327 | 7 |
| 32.70 | 2.74 | 224 | 5 |
| 36.74 | 2.44 | 265 | 6 |
| 38.18 | 2.36 | 175 | 4 |
| 38.38 | 2.34 | 227 | 5 |
| 38.52 | 2.34 | 160 | 4 |
| 39.31 | 2.29 | 142 | 3 |

[a] I/Io = relative intensity.
b. Bold denotes characteristic peak set compared to Form A.

TABLE 9

Peak Positions of Form B shifted XRPD Pattern (file 169284)

| Position (°2θ)[a] | d-spacing | I | I/Io[c] |
|---|---|---|---|
| 6.04 | 14.62 | 102 | 5 |
| 6.49 | 13.61 | 2151 | 100 |
| 7.91 | 11.17 | 240 | 11 |
| 10.92 | 8.10 | 252 | 12 |
| 12.61 | 7.01 | 304 | 14 |
| 12.92 | 6.85 | 263 | 12 |
| 13.10 | 6.75 | 71 | 3 |
| 13.42 | 6.59 | 103 | 5 |
| 13.82 | 6.40 | 177 | 8 |
| 13.99 | 6.32 | 565 | 26 |
| 15.40 | 5.75 | 99 | 5 |
| 15.76 | 5.62 | 1580 | 73 |
| 16.51 | 5.37 | 516 | 24 |
| 17.15 | 5.17 | 334 | 16 |
| 19.92 | 4.45 | 606 | 28 |
| 20.04 | 4.43 | 624 | 29 |
| 21.01 | 4.23 | 101 | 5 |
| 23.92 | 3.72 | 80 | 4 |
| 24.28 | 3.66 | 285 | 13 |
| 24.48 | 3.63 | 81 | 4 |
| 26.77 | 3.33 | 161 | 7 |
| 27.14 | 3.28 | 259 | 12 |
| 27.40 | 3.25 | 1413 | 66 |
| 27.74 | 3.21 | 175 | 8 |
| 28.09 | 3.17 | 122 | 6 |
| 28.82 | 3.10 | 165 | 8 |
| 28.99 | 3.08 | 488 | 23 |
| 31.03 | 2.88 | 118 | 5 |
| 32.58 | 2.75 | 271 | 13 |
| 35.64 | 2.52 | 155 | 7 |
| 35.85 | 2.50 | 329 | 15 |
| 37.48 | 2.40 | 72 | 3 |
| 37.66 | 2.39 | 89 | 4 |
| 38.62 | 2.33 | 84 | 4 |

[a] I/Io = relative intensity.
b. Bold denotes characteristic peak set compared to Form A.

What is claimed is:

1. A solid pharmaceutical composition comprising a crystal form of the compound of formula (I):

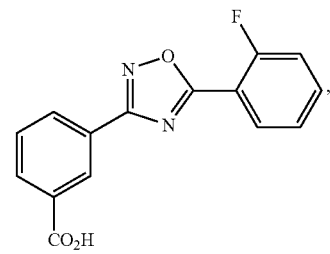

(I)

which has an X-ray powder diffraction pattern comprising at least three peak positions (°2θ±0.2) when measured using Cu Kα radiation, selected from the group consisting of 4.96, 6.39, 10.10, 11.54, 12.62, 12.81, 13.92, 14.16, 14.55, 14.88, 15.07, 15.58, 16.27, 16.61, 18.74, 18.94, 19.28, 19.94, 20.27, 20.74, 20.97, 21.22, 21.93, 22.58, 22.80, 23.00, 23.79, 24.14, 24.46, 25.44, 25.64, 26.07, 26.34, 26.74, 27.06, 27.79, 28.42, 29.09 and 30.48.

2. The pharmaceutical composition of claim 1 further comprising one or more carriers, excipients or diluents.

3. The pharmaceutical composition of claim 2 suitable for oral administration, wherein the pharmaceutical composition is a single unit solid dosage form.

4. The pharmaceutical composition of claim 1, wherein the crystal form has the following unit cell parameters when measured at 150 K: a=24.220 Å; b=3.74640 Å; c=27.4678 Å;

α=90°; β=92.9938°; γ=90°; V=2489.38(17) Å$^3$; Z=8; calculated density ($d_{calc}$, g cm$^{-3}$) is 1.517 g cm$^{-3}$; and the space group is P2$_1$/n (no. 14).

5. The pharmaceutical composition of claim 1, wherein the crystal form has an X-ray powder diffraction pattern comprising at least one peak position (°2θ±0.2) when measured using Cu Kα radiation, selected from the group consisting of 10.10, 11.54, 14.55, 14.88 and 15.07.

6. The pharmaceutical composition of claim 5, wherein the crystal form has a differential scanning calorimetry thermogram which has an endothermic event with a peak temperature at 244° C.

7. The pharmaceutical composition of claim 5, wherein the crystal form has a thermogravimetric analysis thermogram which has a mass loss of less than 1% of the total mass of the sample upon heating from 33° C. to 205° C.

8. The pharmaceutical composition of claim 5, wherein the crystal form is non-hygroscopic.

9. The pharmaceutical composition of claim 1, wherein the crystal form is characterized by $^{13}$C CP/MAS solid-state NMR signals at the following positions: 172.6, 167.0, 131.3, 128.4 and 117.1 ppm, when externally referenced to glycine at 176.5 ppm.

10. The pharmaceutical composition of claim 1, wherein the crystal form is characterized by a $^{13}$C CP/MAS solid-state NMR spectrum as shown in FIG. 4.

11. The pharmaceutical composition of claim 1, wherein the crystal form is pure and has an X-ray powder diffraction pattern comprising peak positions (°2θ±0.2) when measured using Cu Kα radiation, of 10.10, 11.54, 14.55, 14.88 and 15.07.

* * * * *